United States Patent
Ohlmeyer et al.

(10) Patent No.: US 10,450,282 B2
(45) Date of Patent: Oct. 22, 2019

(54) STEREOSPECIFIC PROCESS FOR 3-HETEROCYCLYLCYCLOALIPHATIC-1,2-DIOLS

(71) Applicant: ICAHN SCHOOL OF MEDICINE AT MOUNT SINAI, New York, NY (US)

(72) Inventors: Michael Ohlmeyer, Plainsboro, NJ (US); Nilesh Zaware, Briarwood, NY (US); David Kastrinsky, Fair Lawn, NJ (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 15/750,388

(22) PCT Filed: Aug. 5, 2016

(86) PCT No.: PCT/US2016/045779
§ 371 (c)(1),
(2) Date: Feb. 5, 2018

(87) PCT Pub. No.: WO2017/024229
PCT Pub. Date: Feb. 9, 2017

(65) Prior Publication Data
US 2018/0230112 A1 Aug. 16, 2018

Related U.S. Application Data

(60) Provisional application No. 62/201,819, filed on Aug. 6, 2015.

(51) Int. Cl.
| | |
|---|---|
| C07D 498/04 | (2006.01) |
| C07D 209/86 | (2006.01) |
| C07D 209/88 | (2006.01) |
| C07D 275/06 | (2006.01) |
| C07D 291/08 | (2006.01) |
| C07D 265/38 | (2006.01) |
| C07D 401/04 | (2006.01) |
| C07D 405/04 | (2006.01) |
| C07D 413/04 | (2006.01) |
| C07D 417/04 | (2006.01) |
| C07D 307/30 | (2006.01) |
| C07D 285/01 | (2006.01) |
| C07D 301/14 | (2006.01) |
| C07D 309/28 | (2006.01) |
| C07D 419/04 | (2006.01) |

(52) U.S. Cl.
CPC ......... *C07D 265/38* (2013.01); *C07D 209/86* (2013.01); *C07D 275/06* (2013.01); *C07D 285/01* (2013.01); *C07D 291/08* (2013.01); *C07D 301/14* (2013.01); *C07D 307/30* (2013.01); *C07D 309/28* (2013.01); *C07D 401/04* (2013.01); *C07D 405/04* (2013.01); *C07D 413/04* (2013.01); *C07D 417/04* (2013.01); *C07D 419/04* (2013.01); *C07D 498/04* (2013.01); *C07B 2200/07* (2013.01); *Y02P 20/582* (2015.11)

(58) Field of Classification Search
CPC .................................................. C07D 498/04
See application file for complete search history.

(56) References Cited

U.S. PATENT DOCUMENTS 10,221,152 B2 * 3/2019 Lee .................. A61K 38/21
2018/0251456 A1 * 9/2018 Ohlmeyer et al. ... C07D 413/14

FOREIGN PATENT DOCUMENTS

| WO | WO 2009/095162 | 8/2009 |
| WO | 2013025882 A2 | 2/2013 |
| WO | 2015138500 A1 | 9/2015 |
| WO | WO2015/138496 | 9/2015 |

OTHER PUBLICATIONS

Arnau, et al., Palladium(0)-Catalyzed Allylation of 4(5)-Substituted Imidazoles, 5(6)-Substituted Benzimidazoles, Benzotriazole and 5(6)-Methylbenzotriazole, J. Heterocyclic Chem., vol. 32, pp. 1325-1334, 1995.
Bandini, et al., New Versatile Pd-Catalyzed Alkylation of Indoles via Nucleophilic Allylic Substitution: Controlling the Regioselectivity, Organic Letters, vol. 6, No. 18, pp. 3199-3202, 2004.
Konkel, et al., Palladium-Catalyzed Allylic Coupling of 1,2,3-Triazolo[4,5-*d*]pyrimidines (8-Azapurines), J. Org. Chem., vol. 61, pp. 6199-6204, 1996.
Ramadhar, et al., Stereocontrolled Synthesis of Contiguous C($sp^3$)-C(aryl) Bonds by Lanthanide(III)-Catalyzed Domino Aryl-Claisen [3-3]-Sigmatropic Rearrangements, Organic Letters, vol. 2010, pp. 4446-4449, 2010.
Sato, et al., Stereoselective Total Synthesis of (4S)-*trans*-ß-Elemenone From (S)-2-Cyclohexen-1-OL, Chemistry Letters, pp. 1533-1536, 1983.
Trost, et al., Palladium-Catalyzed Asymmetric Allylic Alkylation of Electron-Deficient Pyrroles with *Meso* Electrophiles, Organic Letters, vol. 14, No. 9, pp. 2254-2257, 2012.
Lu, et al. Metal-Catalyzed Enantioselective Allylation in Asymmetric Synthesis, Agnew Chem. Int. Ed., vol. 47, pp. 258-297, 2008.
International Search Report and Written Opinion issued in PCT/US2016/045779, dated Dec. 20, 2016.
Peter O'Brien et al., cis- and trans-Stereoselective Epoxidation of N-Protected 2-Cyclohexen-1-ylamines; Organic Letters, Nov. 27, 2003, vol. 5, No. 26, pp. 4955-4957.

* cited by examiner

*Primary Examiner* — Susanna Moore
(74) *Attorney, Agent, or Firm* — Heslin Rothenberg Farley & Mesiti, P.C.; Philip Hansen

(57) ABSTRACT

A process for the stereoselective synthesis of chiral 3-heterocyclyl-1,2-dihydroxy cyclohexanes is disclosed. The process involves reacting a tricyclic nitrogenous heterocycle with an allyl carbonate in the presence of a chiral palladium catalyst followed by oxidation of the olefinic bond to provide 3-heterocyclyl-1,2-dihydroxy cyclohexanes, cyclopentanes and corresponding alicyclic heterocycles. Also disclosed are methods for converting the heterocyclyl-1,2-dihydroxy cyclohexanes to 2-amino-6-(heteroaryl)cyclohexanols (and related cyclic compounds).

12 Claims, No Drawings

STEREOSPECIFIC PROCESS FOR 3-HETEROCYCLYLCYCLOALIPHATIC-1,2-DIOLS

CROSS REFERENCE TO RELATED APPLICATIONS

This application is the National Phase filing under 35 U.S.C. § 371 of International Application No. PCT/US2016/045779, filed Aug. 5, 2016, and published as WO 2017/024229 on Feb. 9, 2017, which claims priority from U.S. provisional application 62/201,819, filed Aug. 6, 2015, the entire contents of both of which are incorporated herein by reference.

FIELD OF THE INVENTION

The invention relates to an improved process for the stereoselective synthesis of chiral 3-heterocyclyl-1,2-dihydroxy cyclohexanes, cyclopentanes, their corresponding aliphatic heterocycles and related systems.

BACKGROUND

3-Heterocyclylcyclohexane-1,2-diols (also called 3-heterocyclyl-1,2-dihydroxy cyclohexanes) are key intermediates in the synthesis of certain antineoplastic compounds described in PCT/US2015/019770. An example of such a compound is N-((1R,2R,3S)-2-hydroxy-3-(10H-phenoxazin-10-yl)cyclohexyl)-4-(trifluoromethoxy)benezenesulfonamide, which is described therein. It is obtained from (1S,2R,3S)-3-(10H-phenoxazin-10-yl)cyclohexane-1,2-diol:

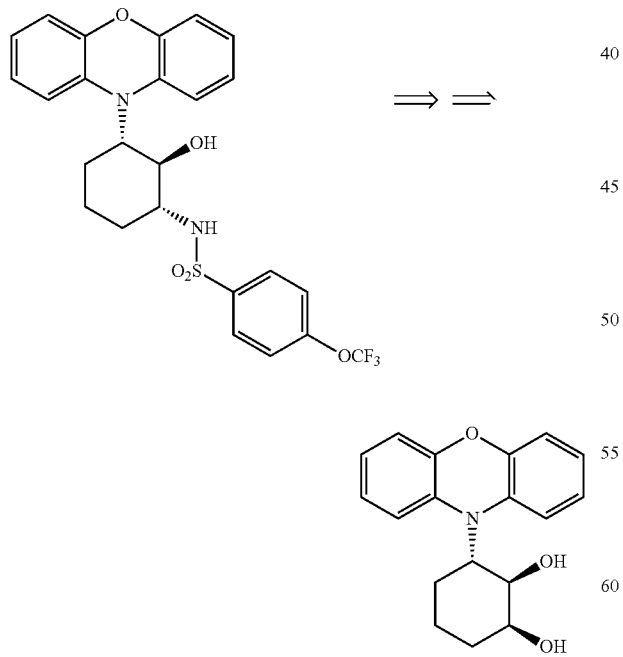

It would be highly desirable to have a process for assembling such 3-heterocyclylcyclohexane-1,2-diols and related species in good yield and high stereoselectivity.

SUMMARY OF THE INVENTION

In a first aspect the invention relates to a process for preparing a substantially enantiomerically pure compound of formula (I):

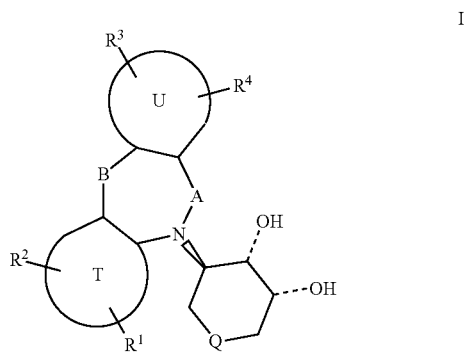

In these compounds:

A is selected from the group consisting of a direct bond, —SO$_2$—, and —C(=O)—;

B is selected from the group consisting of a direct bond, —O—, —SO—, and —SO$_2$—;

T is a benzene ring or a five or six membered heteroaromatic ring;

U is a benzene ring or a five or six membered heteroaromatic ring; and $R^1$, $R^2$, $R^3$ and $R^4$ are chosen independently from H, OH, halogen, cyano, nitro, (C$_1$-C$_3$)alkylamino, (C$_1$-C$_3$)dialkylamino, (C$_1$-C$_3$)acylamino, (C$_1$-C$_3$)alkylsulfonyl, (C$_1$-C$_3$) alkylthio, (C$_1$-C$_3$)alkyl, (C$_1$-C$_3$)haloalkyl, (C$_1$-C$_3$)haloalkoxy, (C$_1$-C$_3$)haloalkylthio, —CC(=O)O(C$_1$-C$_3$)alkyl, and (C$_1$-C$_3$)alkoxy;

Q is chosen from direct bond, —CH$_2$—, —CH$_2$CH$_2$—, —O—, —CH(OH)—, —CH(COOR$^5$)—, —CH(CONR'R")—, —CH(CH$_2$)NR'R", —CH(CN)—, —S(O)$_n$—, —CH(NHBoc), —CH(NHCBZ), —NR$^6$—,

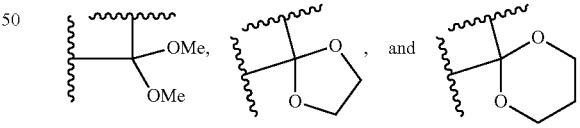

$R^5$ is H or (C$_1$-C$_4$)alkyl;

$R^6$ is chosen from (C$_1$-C$_4$)alkyl, (C$_1$-C$_4$)acyl, (C$_4$-C$_7$) alkoxycarbonyl, and benzyloxycarbonyl;

R' and R" are independently chosen from H, lower alkyl, substituted alkyl, aryl, substituted aryl; or R' and R" together with the nitrogen to which they are attached, may form an optionally substituted heterocyclic ring; and n is zero, one or two.

The process comprises:
(a) reacting a compound of formula II

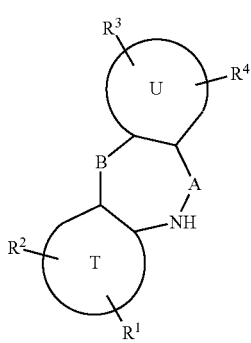

with a compound of formula III

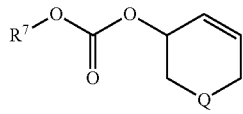

wherein $R^7$ is $(C_1-C_4)$alkyl, in the presence of a chiral palladium catalyst to provide a product of formula IV

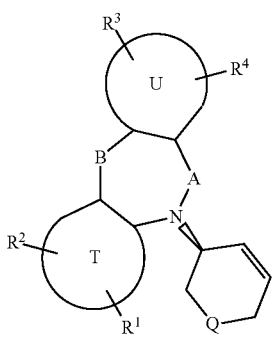

and
(b) oxidizing the product of formula IV with osmium tetroxide to provide I.

In a second aspect, the invention relates to a process for preparing a substantially enantiomerically pure compound of formula V:

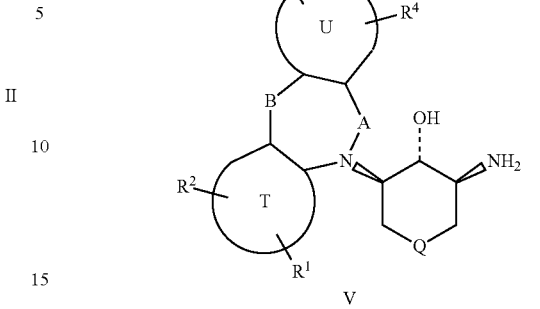

wherein the variables are as defined above, comprising
(a) reacting a diol of formula I

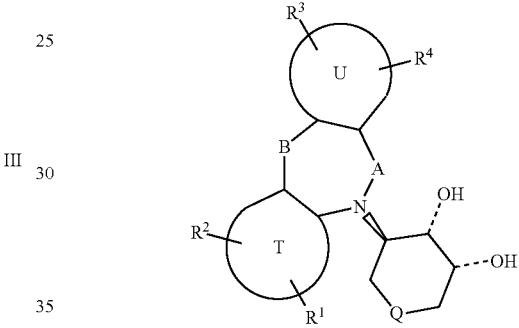

with thionyl chloride or a sulfonyl chloride to provide a sulfonylated product;
(b) reacting the sulfonylated product with an alkali metal azide to provide a rel-(1S,2S,6R)-2-azido-6-(heteroaryl)cyclohexanol of formula VI

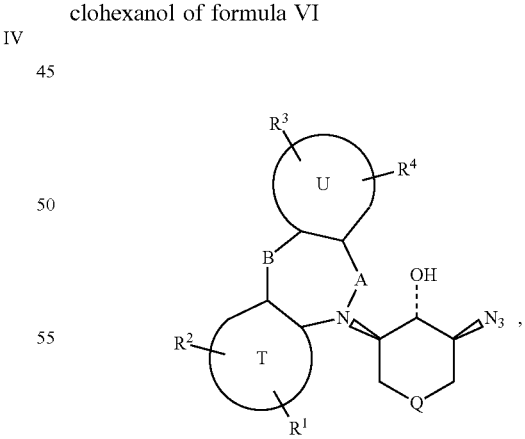

and
(c) reducing the azide of formula VI to a rel-(1S,2S,6R)-2-amino-6-(heteroaryl)cyclohexanol of formula V.

In a third aspect, the invention relates to process for preparing a substantially enantiomerically pure compound of formula (X):

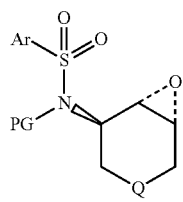

X wherein:

Ar is an optionally substituted benzene or five or six membered heteroaromatic ring;

Q is chosen from direct bond, —CH$_2$—, —CH$_2$CH$_2$—, —O—, —CH(OH)—, —CH(COOR$^5$)—, —CH(CONR'R'')—, —CH(CH$_2$)NR'R'', —CH(CN)—, —CH(NHBoc), —CH(NHCBZ), —NR$^6$—,

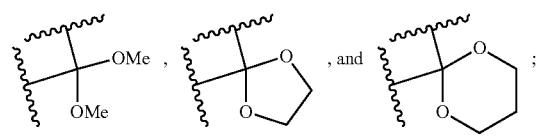 [SMILES: *C(*)(OC)OC ; *C1(*)OCCO1 ; *C1(*)OCCCO1]

and

PG is a protecting group for nitrogen.

The process comprises:

(a) reacting a compound of formula XI

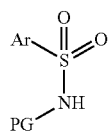

XI with a compound of formula III

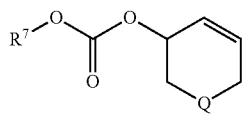

III wherein R$^7$ is (C$_1$-C$_4$)alkyl, in the presence of a chiral palladium catalyst to provide a product of formula XII

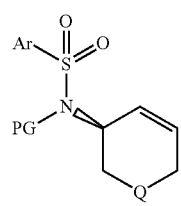

XII and (b) epoxidizing the product of formula XII to provide X.

DETAILED DESCRIPTION OF THE INVENTION

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration. For example, the graphic representation

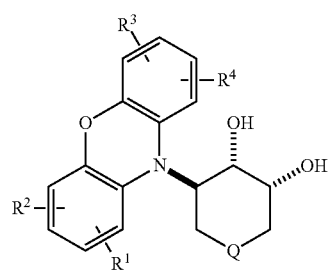

indicates either, or both, of the two cis:trans enantiomers:

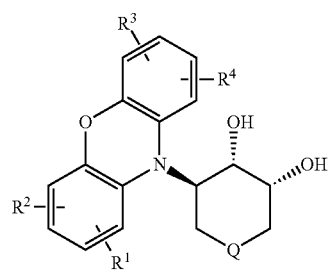

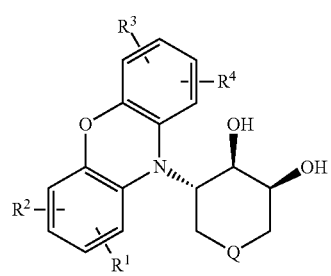

in any ratio, from pure enantiomers to racemates. The graphic representation:

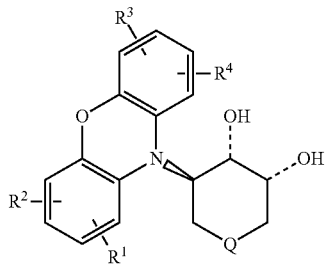

indicates a single enantiomer of unspecified absolute stereochemistry, i.e. it could be either of the two preceding structures, as a substantially pure single enantiomer. And, finally, the representation:

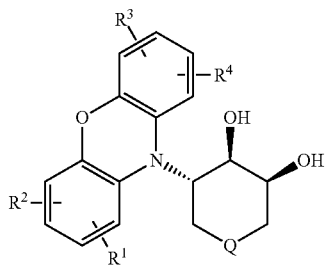

indicates a pure (1S,2R,3S)-3-phenoxazinylcyclohexane-1, 2-diol (when Q is carbon). In the text describing the stereochemistry of the examples, the convention of Chemical Abstracts is used. Thus "rel-(1R,2R,6S)—" indicates that the three chiral centers are in that relative relationship, which would be depicted in a structural diagram by solid bold and dashed lines, whereas "(1R,2R,6S)" without the "rel" indicates a single enantiomer of that absolute configuration, which would be depicted in a structural diagram by solid and broken wedges.

For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Unless otherwise specified, the term "carbocycle" is intended to include ring systems in which the ring atoms are all carbon but of any oxidation state. Thus $(C_3-C_{10})$ carbocycle refers to both non-aromatic and aromatic systems, including such systems as cyclopropane, benzene and cyclohexene; $(C_8-C_{12})$ carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl. When Q is —CH (CONR'R")— or —CH(CH$_2$)NR'R" and R' and R" together with the nitrogen to which they are attached form an optionally substituted heterocyclic ring, exemplary rings include piperidine, morpholine, pyrrolidine, piperazine and the like.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

The term "halogen" means fluorine, chlorine, bromine or iodine atoms. In one embodiment, halogen may be a fluorine or chlorine atom.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonyl amino, alkylsulfinyl, alkyl sulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In preferred embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkyl sulfonyl, alkylsulfonylamino aryl sulfonyl, arylsulfonylamino, and benzyloxy. In some embodiments, substituents are halogen, halo(C$_1$-C$_6$)alkyl, (C$_1$-C$_6$)alkyl, (C$_1$-C$_6$)acyl, hydroxy(C$_1$-C$_6$)alkyl, hydroxy, (C$_1$-C$_6$)alkoxy, halo(C$_1$-C$_6$)alkoxy, aminocarbonyl, carboxy, cyano, acetoxy, nitro, amino, (C$_1$-C$_6$)alkylamino, di(C$_1$-C$_6$)alkylamino, (C$_1$-C$_6$)alkylthio, (C$_1$-C$_6$)alkylsulfinyl, (C$_1$-C$_6$)alkylsulfonyl, (C$_1$-C$_6$)alkylsulfonylamino, and benzyloxy.

Substituents R″ are generally defined when introduced and retain that definition throughout the specification and in all independent claims.

In the first aspect the invention relates to a process for preparing a substantially enantiomerically pure compound of formula (I):

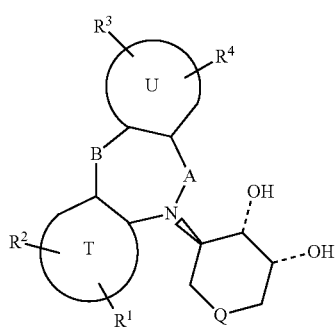

comprising:
(a) reacting a compound of formula II

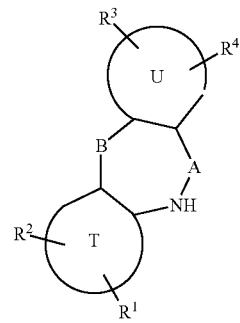

with a compound of formula III

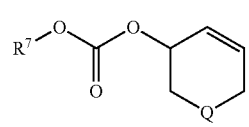

in the presence of a chiral palladium catalyst to provide a product of formula IV

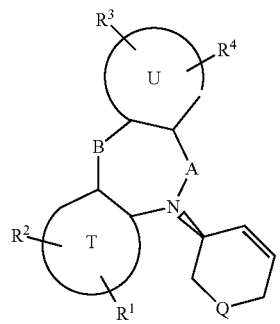

and
(b) oxidizing the product of formula IV with osmium tetroxide to provide I.

In one embodiment, the chiral palladium catalyst is formed from a chiral ligand and a palladium compound. The palladium compound may be chosen from tris(dibenzylideneacetone)dipalladium, bis(dibenzylideneacetone)palladium, tetrakis(triphenylphosphine)palladium, and allylpalladium chloride dimer. In some embodiments, the chiral ligand is chosen from (2,2'-bis(diphenylphosphino)-1,1'-binaphthyl) (BINAP), 5,5'-bis(diphenylphosphino)-4,4'-bi-1,3-benzodioxole (SEGPHOS), 1,2-diaminocyclohexane-N,N'-bis(2-diphenylphosphinobenzoyl) (DACH-phenyl), and 1,2-diaminocyclohexane-N,N'-bis(2-diphenylphosphino-1-naphthoyl) (DACH-naphthyl). Many other palladium compounds and many other ligands that could be used as sources of chiral palladium catalysts are set forth in Lu and Ma, *Angew. Chem. Int. Ed.* 47, 258-297 (2008), the disclosure of which is incorporated herein by reference. Some of the common ligands used in Pd-AAA are:

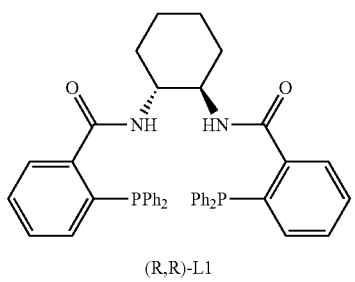

(R,R)-L1

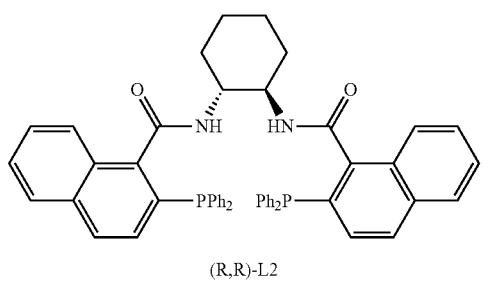

(R,R)-L2

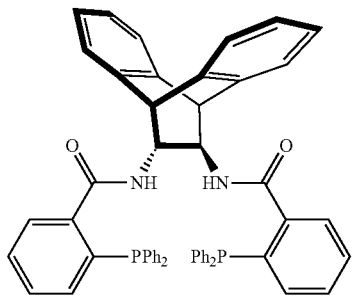

(R,R)-L3

In one embodiment, the chiral palladium catalyst is derived from tris(dibenzylideneacetone)dipalladium and a chiral ligand containing the trans-1,2-diaminocyclohexane (DACH) moiety. In examples below, the catalyst known as (S,S)-DACH-phenyl Trost ligand is used to mediate allylations that resulted in substantially pure (R) chirality at the allylic carbon in the intermediate IV. If (S) chirality is desired, the corresponding (R,R)-DACH-phenyl Trost ligand would be employed. In the examples below, the following two chiral ligands are used and identified as (R,R)-L1 and (S,S)-L1

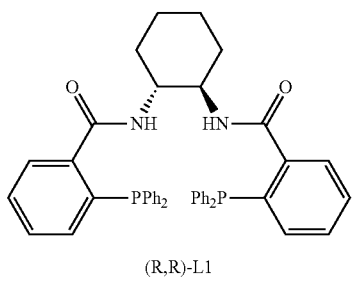

(R,R)-L1

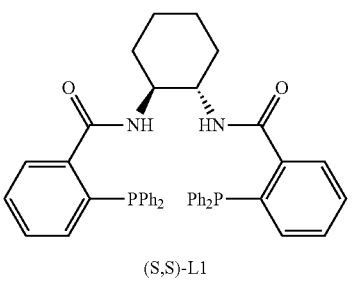

(S,S)-L1

For certain examples, where II is not readily deprotonated, it may be advantageous to run the reaction of II and III in the presence of an added base such as ceasium carbonate, lithium or potassium hexamethyl disilamide, sodamide or lithium diisopropylamide.

The ratio of III to II in the condensation is not critical, but, in the experiments described below, it was found that ratios between 2:1 and 3:1 provided the optimal yields. Ratios below 2:1 are operative, but the yields are often not as high; ratios above 3:1 work as well as those below, but unless starting material is recycled, high ratios would appear to be unattractive for economic, rather than chemical, reasons.

To complete the process, the intermediate IV is oxidized with a reagent that stereoselectively produces a cis diol. The preferred reagent is a catalytic amount of osmium tetroxide with N-methylmorpholine N-oxide as the sacrificial oxidant. One could also employ stoichiometric osmium tetroxide or alkaline permanganate, both of which react in an initial step by a suprafacial cycloaddition mechanism. The result is a substantially enantiomerically pure 1,2,3-tri substituted diol of the formula:

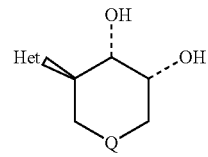

The foregoing process steps are carried out in the liquid phase, so solvents will be employed. No criticality has been observed in the choice of solvents. Generally the first step of palladium allylation is carried out in aprotic solvents and the second step, oxidation, is carried out in protic solvents. Similarly, no criticality has been observed in the reaction temperature. Generally it is convenient to run them at ambient temperature, but temperatures between 0° C. and 100° C. will be found suitable.

The diol is converted to products of the genus disclosed in PCT/US2015/019770 via an intermediate rel-(1S,2S,6R)-2-amino-6-(heterocyclyl)cyclohexanol of formula V:

by one of two alternate pathways.

The diol of formula I

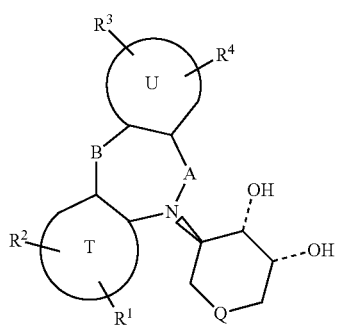

may be reacted with thionyl chloride or a sulfonyl chloride to provide a sulfonylated product; and the sulfonylated product may be reacted with an alkali metal azide to provide a rel-(1S,2S,6R)-2-azido-6-(heteroaryl)cyclohexanol of formula VI:

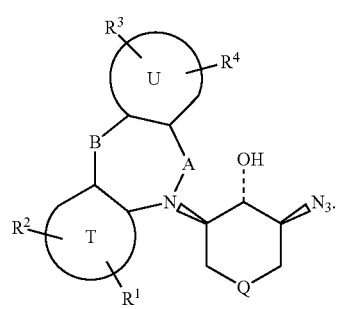

The azide may be reduced to provide the rel-(1S,2S,6R)-2-amino-6-(heteroaryl)cyclohexanol of formula V. When the diol of formula I is reacted with thionyl chloride, a dioxathiole of formula VII results:

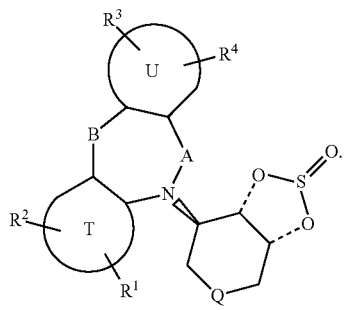

When the diol of formula I is reacted with methanesulfonyl chloride, a sulfonate of formula VIII results:

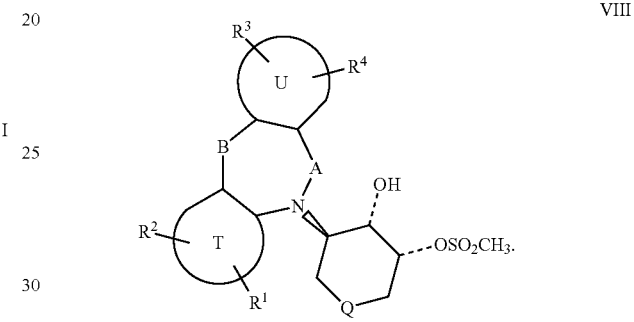

Either of these may be treated with an azide, such as sodium azide, to provide the a rel-(1S,2S,6R)-2-azido-6-(heterocyclyl)cyclohexanol of formula VI

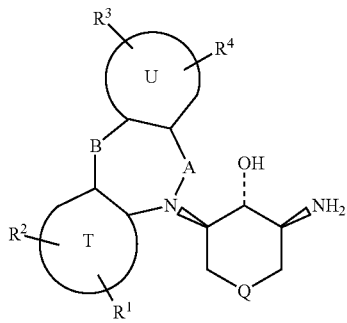

which is reduced to a rel-(1S,2S,6R)-2-amino-6-(heterocyclyl)cyclohexanol of formula V.

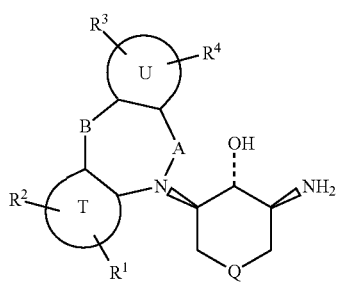

A convenient reducing agent is triphenyl phosphine, but there are many procedures known to persons of skill that may be employed for reducing an azide to an amine.

When Q is a ketal or cyclic ketal, e.g.

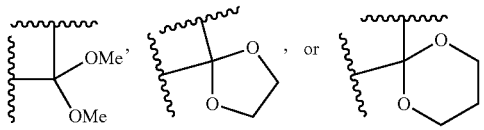 [SMILES: *C(*)(OC)OC ; "," ; *C1(*)OCCO1 ; "," ; "or" ; *C1(*)OCCCO1]

the starting material may be prepared as follows:

Known 1,4-dioxaspiro[4.5]dec-8-en-7-ol is prepared according to Zhang and Koreeda, Organic Letters, Vol. 4, No. 21, pages 3755-3758 (2002). To a solution of 1,4-dioxaspiro[4.5]dec-8-en-7-ol (1.0 equivalent) in THF is cooled to −78° C., n-butyllithium (1.2 equivalents, 2.5 M in hexanes) is added. The resulting solution is warmed to 0° C. and stirred for 5 min prior to addition of di-tert-butyl dicarbonate (2.0 equivalents) in THF. The reaction is warmed to RT, stirred for 16 h. The reaction is then quenched with water, extracted with ethyl acetate, washed with brine, concentrated, and the residue is purified by column chromatography (SiO$_2$, increasing gradient of ethyl acetate in hexanes) to give tert-butyl (1,4-dioxaspiro[4.5]dec-8-en-7-yl) carbonate.

Using the typical procedure, 9H-carbazole is reacted with tert-butyl (1,4-dioxaspiro[4.5]dec-8-en-7-yl) carbonate (1.20 mmol) in presence of (R,R)-DACH and Pd$_2$dba$_3$.CHCl$_3$ for 10 days to afford (S)-9-(1,4-dioxaspiro[4.5]dec-8-en-7-yl)-9H-carbazole in 5% to >90% yield and enantiomeric excess of 10% to >99%. Using the typical procedure (S)-9-(1,4-dioxaspiro[4.5]dec-8-en-7-yl)-9H-carbazole is dihydroxylated to (7S,8R,9S)-9-(9H-carbazol-9-yl)-1,4-dioxaspiro[4.5]decane-7,8-diol 5% to >90% yield and enantiomeric excess of 10% to >99%:

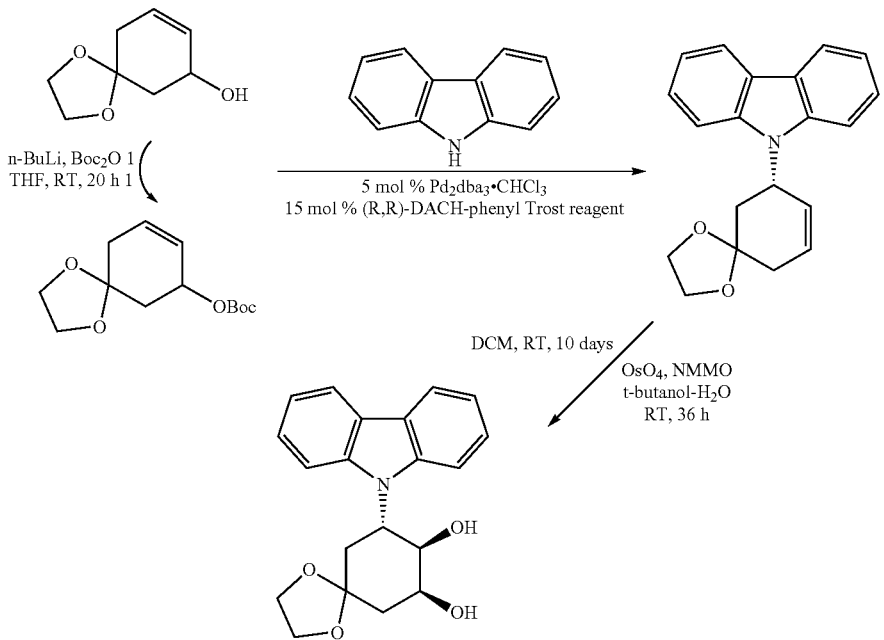

Compounds in the other enantiomeric series may be accessed by the use of (S,S)-DACH.

Enantiomerically enriched 10-(1,4-dioxaspiro[4,5]dec-8-en-7-yl)-1 OH-phenoxazine and 9-(10H-phenoxazin-10-yl)-1,4-dioxaspiro[4.5]decane-7,8-diol may be obtained in by using phenoxazine in the place of carbazole in the above allylation with tert-butyl (1,4-dioxaspiro[4.5]dec-8-en-7-yl) carbonate.

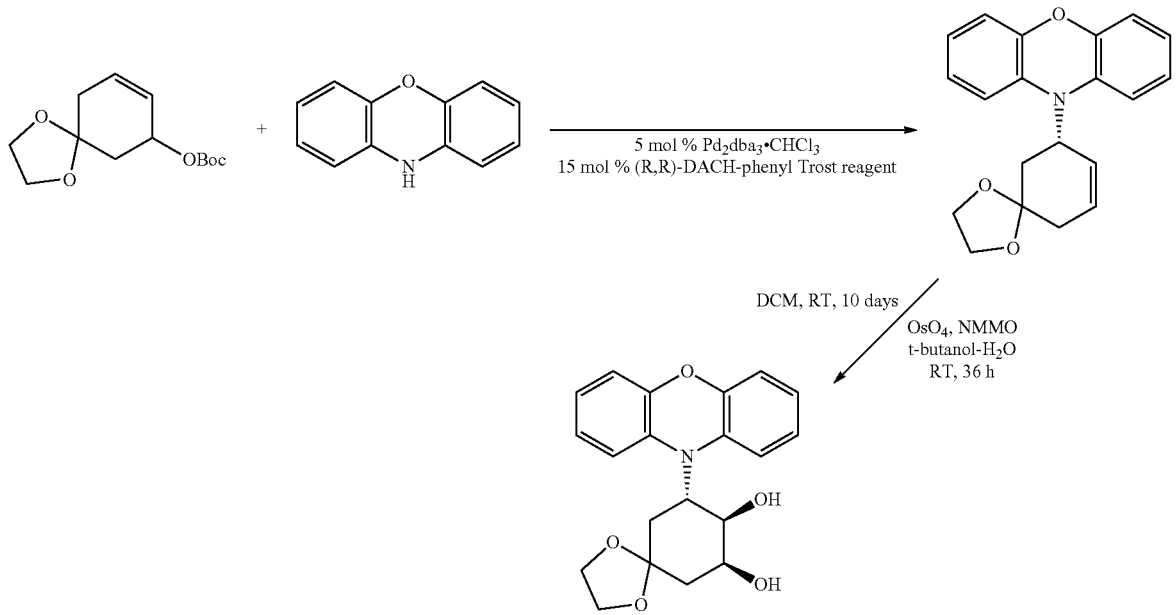

Substituted tricylic systems may be obtained by using the appropriately substituted (eg F, Cl or CF$_3$) carbazoles or phenoxazines.

Compounds in which Q forms a cyclohexane ring with a C-attached carboxamide; —CH(CONR'R")— may be obtained via carboxamido substituted cycloalkene carbonates. Carboxamido substituted cycloalkene carbonates may be conveniently accessed by reaction of commercially available 6-oxabicyclo[3.2.1]oct-3-en-7-one with amines, HNR'R". The reaction involves reacting 6-oxabicyclo[3.2.1] oct-3-en-7-one with amines or anilines in a polar solvent, optionally in the presence of an added base, with conventional or microwave heating to form the pendant amide and allylic alcohol. The allylic alcohol functionality is activated by carbonate formation in a manner similar to other examples to give intermediates which are subjected to the palladium mediated alkylation conditions described above in the in the presence of nucleophiles to give cycloalkene intermediates. These may be dihydroxylated using conditions described above.

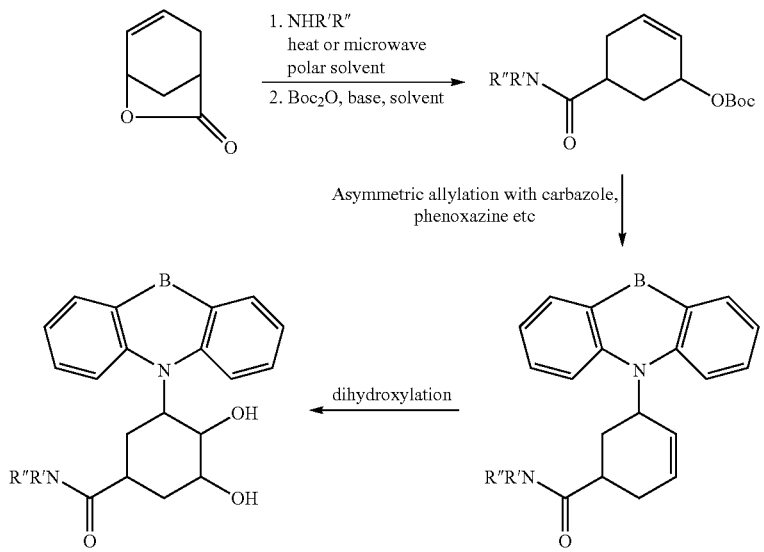

For example, compounds in which B is a direct bond, B is an oxygen and B is —CH$_2$CH$_2$— can be made by this process, and compounds in which R'R" represents a cyclic structure (e.g. morpholine, piperidine and piperazine) are similarly available.

Compounds in which Q froms a piperidine may be synthesized similarly from tert-butyl 5-(((tert-butoxycarbonyl)oxy)-5,6-dihydropyridine-1(2H)-carboxylate:

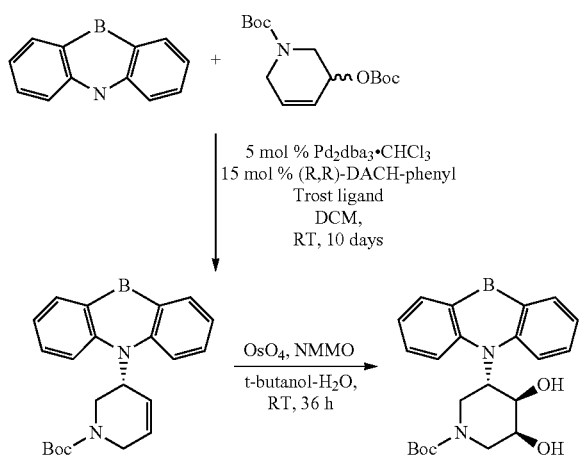

Example 1. Synthesis of (1R,2S,3R)-3-(10H-phenoxazin-10-yl)cyclohexane-1,2-diol

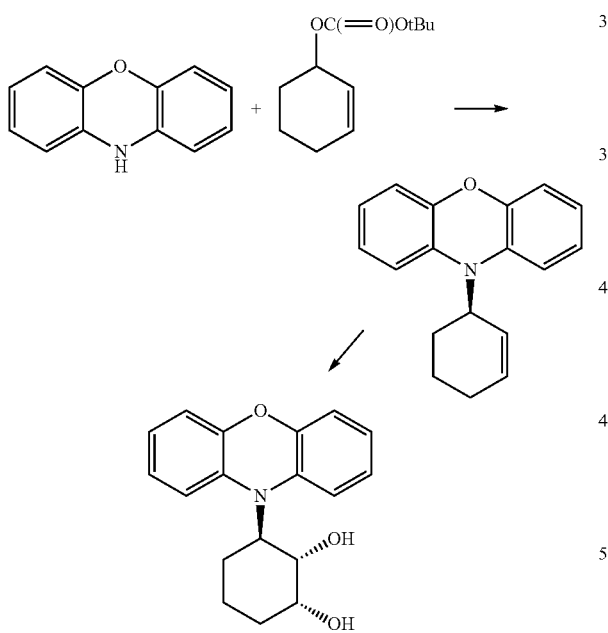

Example 1

A 20 mL Biotage® microwave reaction vial was charged with $Pd_2.dba_3 \cdot CHCl_3$ (0.052 g, 0.05 mmol), and (S,S)-DACH-phenyl Trost ligand (0.104 g, 0.15 mmol). The vial was sealed, evacuated and backfilled with argon three times. Dry degassed dichloromethane (2.5 mL) was added to this vial, and the mixture was stirred at room temperature for 30 min. Racemic tert-butyl cyclohex-2-en-1-yl carbonate (0.238 g, 1.20 mmol) was added to the vial and the contents were transferred to a separate 20 mL Biotage® microwave reaction vial containing 10H-phenoxazine (0.183 g, 1.00 mmol) in dry degassed dichloromethane (3.0 mL). The reaction mixture was stirred at room temperature for 10 days. At this point, the reaction mixture was evaporated onto silica gel and subjected to column chromatography ($SiO_2$; 100% hexanes) to afford pure (R)-10-(cyclohex-2-en-1-yl)-10H-phenoxazine (0.114 g, 43%). HRMS m/z 264.1383 ([M+H$^+$], $C_{18}H_{18}NO$ requires 264.1379).

A solution of (R)-10-(cyclohex-2-en-1-yl)-10H-phenoxazine (0.114 g, 0.432 mmol), 4-methylmorpholine N-oxide monohydrate (0.056 g, 0.476 mmol), and osmium tetroxide (0.040 mL, 0.004 mmol, 2.5% in tert-butanol) in tert-butanol (1.30 mL) and water (0.30 mL), was stirred at RT for 34 h. The reaction mixture was treated with solid sodium bisulfate solution, stirred for 1 h, evaporated on to silica and purified by flash chromatography ($SiO_2$, 0%-70% ethyl acetate-hexanes) to afford (1R,2S,3R)-3-(10H-phenoxazin-10-yl)cyclohexane-1,2-diol (Example 1) (0.101 g, 79%). $^1$H NMR (600 MHz, MeOD) δ 7.01-7.00 (2H, m), 6.88 (2H, bs), 6.80 (2H, m), 6.73-6.72 (2H, m), 4.14 (1H, m), 4.04-4.03 (1H, m), 3.90 (1H, bs), 1.93 (1H, bs), 1.84-1.74 (3H, m), 1.53-1.52 (2H, m); $^{13}$C NMR (150 MHz, MeOD) δ 123.3, 122.3, 118.7, 115.3, 72.2, 70.6, 64.3, 30.8, 28.7, 19.1; HRMS m/z 298.1437 ([M+H$^+$], $C_{18}H_{20}NO_3$ requires 298.1438). Material produced in this fashion exhibited $[\alpha]_D$=+0.03 (c=1.0, $CH_2Cl_2$). The enantiomeric identity and purity was also confirmed by analytical chiral HPLC >99% (CHIRALPAK® IF-3 column, 70:30 hexanes-EtOH, 1.5 mL/min, retention times: 4.66 min Example 2. Synthesis of (1R,2S,3R)-3-(9H-carbazol-9-yl)cyclohexane-1,2-diol

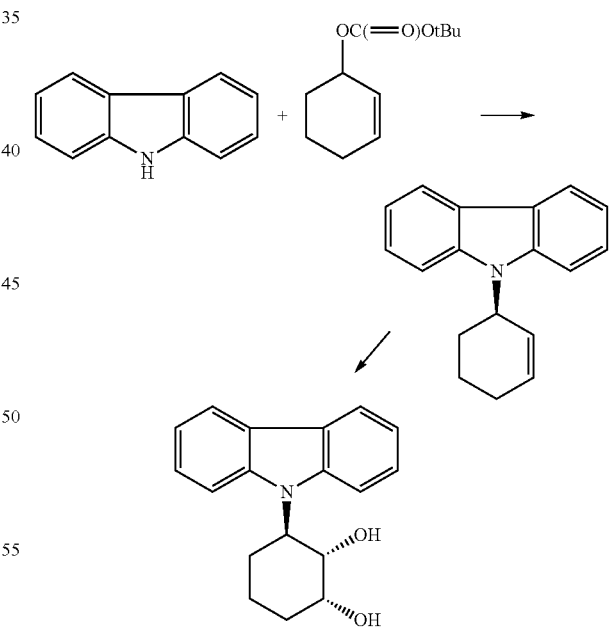

Example 2

A 20 mL Biotage® microwave reaction vial was charged with $Pd_2.dba_3 \cdot CHCl_3$ (0.052 g, 0.05 mmol), and (S,S)-DACH-phenyl Trost ligand (0.104 g, 0.15 mmol). The vial was sealed and backfilled with argon three times. Dry degassed dichloromethane (2.5 mL) was added to this vial, and the mixture was stirred at room temperature for 30 min. Racemic tert-butyl cyclohex-2-en-1-yl carbonate (0.238 g, 1.2 mmol) was added to the vial and the contents were transferred to a separate 20 mL Biotage® microwave reaction vial containing 9H-carbazole 3 (0.167 g, 1.00 mmol) in dry degassed dichloromethane (3.0 mL). The reaction mixture was stirred at room temperature for 10 days. At this point, the reaction mixture was evaporated onto silica gel and subjected to column chromatography (SiO$_2$; 100% hexanes) to afford pure (R)-9-(cyclohex-2-en-1-yl)-9H-carbazole (0.082 g, 33%). $^1$H NMR (600 MHz, MeOD) δ 8.05-8.04 (2H, m), 7.55 (2H, bs), 7.36 (2H, bs), 7.15 (2H, bs), 6.08 (1H, bs), 5.86 (1H, bs), 5.39 (1H, bs), 2.31-2.17 (3H, m), 1.99-1.92 (3H, m); $^{13}$C NMR (150 MHz, MeOD) δ 140.0, 130.5, 128.8, 125.1, 123.2, 119.7, 118.5, 109.9, 51.7, 27.2, 24.5, 21.8; HRMS m/z 248.1434 ([M+H$^+$], C$_{18}$H$_{18}$N requires 248.1436).

A solution of (R)-9-(cyclohex-2-en-1-yl)-9H-carbazole (0.035 g, 0.142 mmol), 4-methylmorpholine N-oxide monohydrate (0.018 g, 0.156 mmol), and osmium tetroxide (0.016 mL, 0.001 mmol, 2.5% in tert-butanol) in tert-butanol (1.00 mL) and water (0.10 mL), was stirred at RT for 60 h. The reaction mixture was treated with solid sodium bisulfite solution, stirred for 1 h, evaporated on to silica and purified by flash chromatography (SiO$_2$, 0%-70% ethyl acetate-hexanes) to afford (1R,2S,3R)-3-(9H-carbazol-9-yl)cyclohexane-1,2-diol (Example 2) (0.037 g, 95%). $^1$H NMR (600 MHz, MeOD) δ 8.07 (2H, d, J=6.6 Hz), 7.65-7.63 (2H, m), 7.40 (2H, d, J=7.2 Hz), 7.16 (2H, d, J=7.8 Hz), 4.55 (1H, dd, J=10.8, 3 Hz), 4.23 (1H, d, J=2.4 Hz), 2.51-2.44 (1H, m), 2.03-1.96 (2H, m), 1.88-1.77 (3H, m), 1.70-1.67 (1H, m); $^{13}$C NMR (150 MHz, MeOD) δ 125.1, 119.7, 118.3, 71.0, 70.5, 55.3, 31.1, 28.8, 19.1; LCMS m/z 282.2184 ([M+H$^+$], C$_{18}$H$_{20}$NO$_2$ requires 282.1489). Material produced in this fashion exhibited [α]$_D$=+0.43 (c=1.0, CH$_2$Cl$_2$). The enantiomeric identity and purity was also confirmed by analytical chiral HPLC >99% (CHIRALPAK® IF-3 column, 70:30 hexanes-EtOH, 1.5 mL/min, retention times: 5.19 min Example 2a. Second Synthesis of (1R,2S,3R)-3-(9H-carbazol-9-yl)cyclohexane-1,2-diol A 20 mL Biotage® microwave reaction vial was charged with Pd$_2$dba$_3$. CHCl$_3$ (0.052 g, 0.05 mmol), and (S,S)-DACH-phenyl Trost ligand (0.104 g, 0.15 mmol). The vial was sealed, evacuated and backfilled with argon three times. Dry degassed dichloromethane (2.5 mL) was added to this vial, and the mixture was stirred at room temperature for 30 min. Racemic tert-butyl cyclohex-2-en-1-yl carbonate (0.238 g, 1.2 mmol) was added to the vial and the contents were transferred to a separate 20 mL Biotage® microwave reaction vial containing 9H-carbazole 3 (0.167 g, 1.00 mmol) in dry degassed dichloromethane (3.0 mL). The reaction mixture was stirred at 50° C. for 18 h. At this point, the reaction mixture was evaporated onto silica gel and subjected to column chromatography (SiO$_2$; 100% hexanes) to afford pure (R)-9-(cyclohex-2-en-1-yl)-9H-carbazole 0.092 g, 37%). HRMS m/z 248.1434 ([M+H$^+$], C$_{18}$H$_{18}$N requires 248.1436).

A solution of (R)-9-(cyclohex-2-en-1-yl)-9H-carbazole (0.090 g, 0.363 mmol), 4-methylmorpholine N-oxide monohydrate (0.047 g, 0.401 mmol), and osmium tetroxide (0.036 mL, 0.004 mmol, 2.5% in tert-butanol) in tert-butanol (1.00 mL) and water (0.10 mL), was stirred at RT for 60 h. The reaction mixture was treated with solid sodium bisulfite solution, stirred for 1 h, evaporated on to silica and purified by flash chromatography (SiO$_2$, 0%-70% ethyl acetate-hexanes) to afford (1R,2S,3R)-3-(9H-carbazol-9-yl)cyclohexane-1,2-diol (Example 2a) (0.096 g, 95%). $^1$H NMR (600 MHz, MeOD) δ 8.07 (2H, d, J=6.6 Hz), 7.64 (2H, bs), 7.39 (2H, d, J=7.2 Hz), 7.16 (2H, d, J=7.8 Hz), 4.55 (1H, dd, J=10.8, 3 Hz), 4.23 (1H, bs), 2.51-2.44 (1H, m), 2.03-1.96 (2H, m), 1.88-1.78 (3H, m), 1.70-1.67 (1H, m); $^{13}$C NMR (150 MHz, MeOD) δ 125.1, 119.8, 118.3, 109.1, 71.0, 70.5, 55.3, 31.1, 28.8, 19.1; LCMS m/z 282.2717 ([M+H$^+$], C$_{18}$H$_{20}$NO$_2$ requires 282.1489). Material produced in this fashion exhibited [α]$_D$=+0.39 (c=1.0, CH$_2$Cl$_2$). The enantiomeric identity and purity was also confirmed by analytical chiral HPLC 92.4% (CHIRALPAK® IF-3 column, 70:30 hexanes-EtOH, 1.5 mL/min, retention times: 5.22 min Examples 3, 4 and 5. Synthesis of rel-(3R,4S,5R)-5-(10H-phenoxazin-10-yl)tetrahydro-2H-pyran-3,4-diol (3); (3S,4R,5S)-5-(10H-phenoxazin-10-yl)tetrahydro-2H-pyran-3,4-diol (4); and (3R,4S,5R)-5-(10H-phenoxazin-10-yl)tetrahydro-2H-pyran-3,4-diol (5)

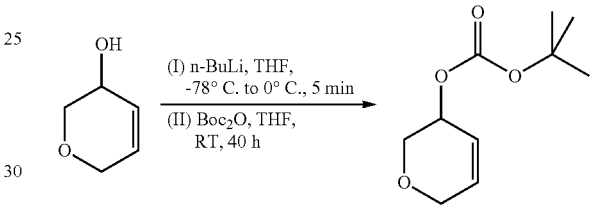

Tert-butyl (3,6-dihydro-2H-pyran-3-yl) carbonate: To a solution of 3,6-dihydro-2H-pyran-3-ol (1.00 g, 9.98 mmol) in THF (33 mL) was added n-butyllithium (2.5 M in hexanes, 3.95 mL, 9.98 mmol) at −78° C. The resulting solution was warmed to 0° C. and stirred for 5 min prior to addition of di-tert-butyl dicarbonate (2.38 g, 10.9 mmol) in THF (17 mL). The reaction was warmed to RT, stirred for 40 h. The reaction was then quenched with water, extracted with ethyl acetate, washed with brine, concentrated, and the residue purified by flash chromatography (SiO$_2$, 0%-3% ethyl acetate-hexanes) to afford tert-butyl (3,6-dihydro-2H-pyran-3-yl) carbonate (1.39 g, 70%) as a colorless oil. $^1$H NMR (600 MHz, CDCl$_3$) δ 6.04 (1H, d, J=10.2 Hz), 5.94-5.92 (1H, m), 4.88 (1H, bs), 4.19-4.16 (1H, m), 4.06-4.03 (1H, m), 3.93-3.91 (1H, m), 3.80 (1H, dd, J=12.6, 1.8 Hz), 1.46 (9H, s); $^{13}$C NMR (150 MHz, MeOD) δ 153.2, 132.4, 122.4, 82.4, 67.5, 65.1, 41.7, 27.9.

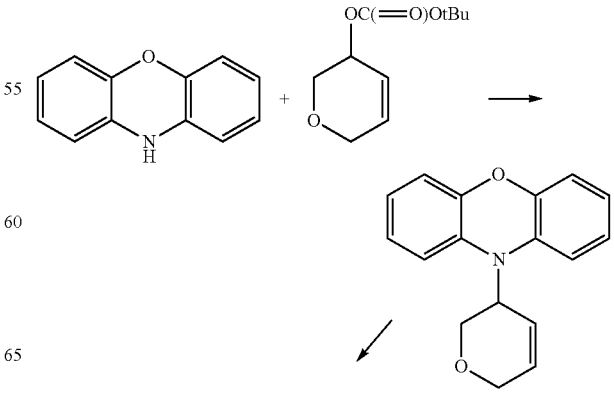

-continued

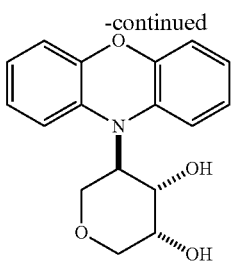

Example 3

Example 3. 5-(10H-phenoxazin-10-yl)tetrahydro-2H-pyran-3,4-diol

A 20 mL Biotage® microwave reaction vial (Vial A) was charged with $Pd_2.dba_3$.$CHCl_3$ (0.103 g, 0.10 mmol), and triphenylphosphine (0.078 g, 0.30 mmol). The vial was sealed, evacuated and backfilled with argon three times. Dry degassed THF (6.00 mL) was added to this vial, and the mixture was stirred at room temperature for 60 min. In a separate 20 mL Biotage® microwave reaction vial (Vial B), 10H-phenoxazine (0.366 g, 2.00 mmol) was added. The vial was sealed, evacuated and backfilled with argon three times. Dry degassed THF (5.00 mL) was added, and Potassium bis(trimethylsilyl)amide solution (1.0 M in THF, 1.00 mL, 2.00 mmol) was added drop wise at RT and the mixture was stirred for 60 min. Following this tert-butyl (5,6-dihydro-2H-pyran-2-yl) carbonate (0.960 g, 4.80 mmol), and the contents of vial B were transferred to vial A in this sequence. The reaction mixture was stirred at room temperature for 14 h. At this point, the reaction mixture was evaporated onto silica gel and purified by flash chromatography ($SiO_2$, 0%-5% ethyl acetate-hexanes) to afford crude 10-(3,6-dihydro-2H-pyran-3-yl)-10H-phenoxazine (0.442 g), which was taken to the next step without further purification. LCMS m/z 266.1203 ([M+H$^+$], $C_{17}H_{16}NO_2$ requires 266.1176).

A solution of 10-(3,6-dihydro-2H-pyran-3-yl)-10H-phenoxazine (0.398 g, 1.50 mmol), 4-methylmorpholine N-oxide (0.386 g, 3.30 mmol), and osmium tetroxide (0.320 mL, 0.030 mmol, 2.5% in tert-butanol) in tert-butanol (2.0 mL) and water (0.4 mL), was stirred at RT for 36 h. The reaction mixture was treated with solid sodium bisulfite for 1 h, dichloromethane and silica were added, the mixture was concentrated and purified by flash chromatography ($SiO_2$, 20%-66% ethyl acetate-hexanes) to afford rel-(3R,4S,5R)-5-(10H-phenoxazin-10-yl)tetrahydro-2H-pyran-3,4-diol (Example 3) (0.235 g, 52% over two steps). $^1$H NMR (600 MHz, MeOD) δ 7.00-6.98 (2H, m), 6.91-6.89 (2H, m), 6.83-6.81 (2H, m), 6.74 (2H, dd, J=8.4, 1.2 Hz), 4.26 (1H, dd, J=10.2, 3.0 Hz), 4.10-4.03 (2H, m), 3.93 (1H, bs), 3.89 (1H, d, J=12.6 Hz), 3.75 (1H, t, J=10.8 Hz), 3.58 (1H, d, J=12.6 Hz); $^{13}$C NMR (150 MHz, MeOD) δ 149.5, 135.4, 123.4, 122.6, 118.3, 115.5, 71.0, 70.2, 68.7, 68.4, 62.5; HRMS calcd for $C_{17}H_{18}NO_4$ [M+H$^+$] 300.1230, found 300.1203.

Example 4. (3S,4R,5S)-5-(10H-phenoxazin-10-yl)tetrahydro-2H-pyran-3,4-diol

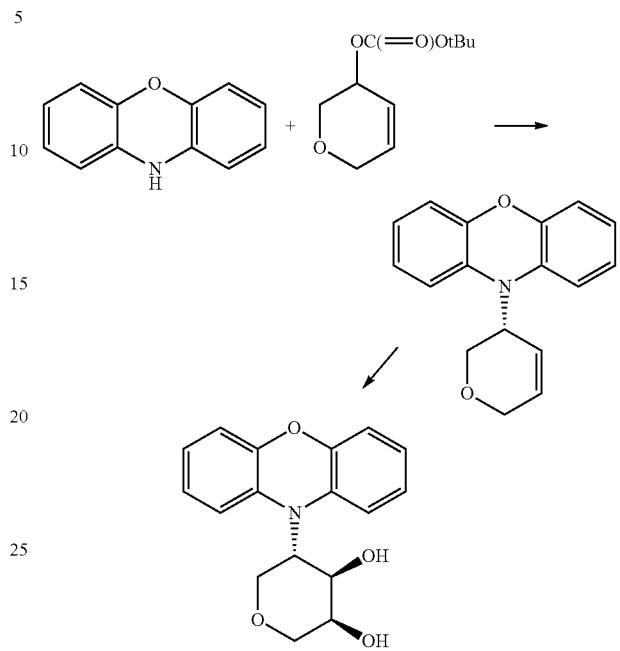

Example 4

A 20 mL Biotage® microwave reaction vial was charged with $Pd_2.dba_3$.$CHCl_3$ (0.103 g, 0.10 mmol), and (R,R)-DACH-phenyl Trost ligand (0.207 g, 0.30 mmol). The vial was sealed, evacuated and backfilled with argon three times. Dry degassed dichloromethane (6.0 mL) was added to this vial, and the mixture was stirred at room temperature for 60 min. Tert-butyl cyclohex-2-en-1-yl carbonate (0.960 g, 4.80 mmol) was added to the vial and the contents were transferred to a separate 20 mL Biotage® microwave reaction vial containing 10H-phenoxazine (0.366 g, 2.00 mmol) in dry degassed dichloromethane (5.0 mL). The reaction mixture was stirred at room temperature for 10 days. At this point, the reaction mixture was evaporated onto silica gel and subjected to flash chromatography ($SiO_2$; 0%-5% ethylacetate-hexanes) to afford crude (R)-10-(cyclohex-2-en-1-yl)-10H-phenoxazine (0.538 g), which was taken to the next step without further purification. LCMS m/z 266.1155 ([M+H$^+$], $C_{17}H_{16}NO_2$ requires 266.1176).

A solution of (R)-10-(cyclohex-2-en-1-yl)-10H-phenoxazine (0.538 g, 2.02 mmol), 4-methylmorpholine N-oxide (0.522 g, 4.46 mmol), and osmium tetroxide (0.410 mL, 0.040 mmol, 2.5% in tert-butanol) in tert-butanol (2.70 mL) and water (0.54 mL), was stirred at RT for 60 h. The reaction mixture was treated with solid sodium bisulfate for 1 h, dichloromethane and silica were added, the mixture was concentrated and purified by flash chromatography ($SiO_2$, 20%-66% ethyl acetate-hexanes) to afford (3S,4R,5S)-5-(10H-phenoxazin-10-yl)tetrahydro-2H-pyran-3,4-diol (Example 4) (0.492 g, 82% over two steps).

$^1$H NMR (600 MHz, MeOD) δ 6.99-6.98 (2H, m), 6.90 (2H, td, J=7.2, 0.6 Hz), 6.83-6.81 (2H, m), 6.74 (2H, dd, J=7.8, 0.6 Hz), 4.25 (1H, dd, J=10.2, 3.0 Hz), 4.10-4.03 (2H, m), 3.93 (1H bs), 3.89 (1H, d, J=12.6 Hz), 3.75 (1H, t, J=10.8 Hz), 3.57 (1H, d, J=12.0 Hz); $^{13}$C NMR (150 MHz,

MeOD) δ 149.5, 135.4, 123.4, 122.6, 118.3, 115.5, 71.0, 70.2, 68.7, 68.4, 62.5; ESI-HRMS calcd for $C_{17}H_{18}NO_4$ [M+H$^+$] 300.1230, found 300.1202. Material produced in this fashion exhibited $[\alpha]_D$=+0.30 (c=1.0, $CH_2Cl_2$).

Example 5. (3R,4S,5R)-5-(10H-phenoxazin-10-yl)tetrahydro-2H-pyran-3,4-diol

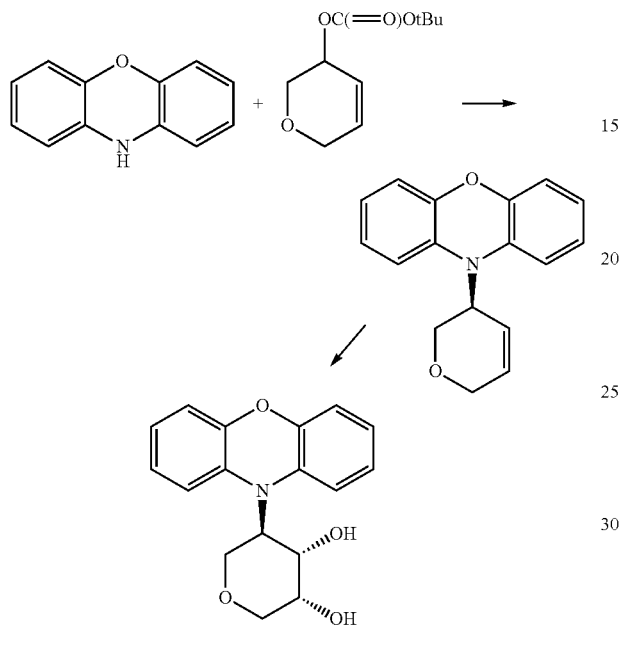

Example 5

A 20 mL Biotage® microwave reaction vial was charged with $Pd_2.dba_3 \cdot CHCl_3$ (0.103 g, 0.10 mmol), and (S,S)-DACH-phenyl Trost ligand (0.207 g, 0.30 mmol). The vial was sealed, evacuated and backfilled with argon three times. Dry degassed dichloromethane (6.0 mL) was added to this vial, and the mixture was stirred at room temperature for 60 min. Tert-butyl cyclohex-2-en-1-yl carbonate (0.960 g, 4.80 mmol) was added to the vial and the contents were transferred to a separate 20 mL Biotage® microwave reaction vial containing 10H-phenoxazine (0.366 g, 2.00 mmol) in dry degassed dichloromethane (5.0 mL). The reaction mixture was stirred at room temperature for 10 days. At this point, the reaction mixture was evaporated onto silica gel and subjected to flash chromatography ($SiO_2$; 0%-5% ethylacetate-hexanes) to afford crude (S)-10-(cyclohex-2-en-1-yl)-10H-phenoxazine (0.550 g), which was taken to the next step without further purification. LCMS m/z 266.1465 ([M+H$^+$], $C_{17}H_{16}NO_2$ requires 266.1176).

A solution of (S)-10-(cyclohex-2-en-1-yl)-10H-phenoxazine (0.550 g, 2.07 mmol), 4-methylmorpholine N-oxide (0.534 g, 4.56 mmol), and osmium tetroxide (0.420 mL, 0.040 mmol, 2.5% in tert-butanol) in tert-butanol (2.75 mL) and water (0.55 mL), was stirred at RT for 60 h. The reaction mixture was treated with solid sodium bisulfite for 1 h, dichloromethane and silica were added, the mixture was concentrated and purified by flash chromatography ($SiO_2$, 20%-66% ethyl acetate-hexanes) to afford (3R,4S,5R)-5-(10H-phenoxazin-10-yl)tetrahydro-2H-pyran-3,4-diol (0.483 g, 81% over two steps). $^1$H NMR (600 MHz, MeOD) δ 6.99-6.98 (2H, m), 6.90 (2H, td, J=7.8, 1.2 Hz), 6.83-6.81 (2H, m), 6.74 (2H, dd, J=7.8, 1.2 Hz), 4.25 (1H, dd, J=10.2, 3.0 Hz), 4.10-4.03 (2H, m), 3.93 (1H, bs), 3.89 (1H, d, J=12.6 Hz), 3.75 (1H, t, J=10.8 Hz), 3.57 (1H, d, J=12.0 Hz); $^{13}$C NMR (150 MHz, MeOD) δ 149.5, 135.4, 123.4, 122.6, 118.3, 115.5, 71.0, 70.2, 68.7, 68.4, 62.5; ESI-HRMS calcd for $C_{17}H_{18}NO_4$ [M+H$^+$] 300.1230, found 300.1227. Material produced in this fashion exhibited $[\alpha]_D$=−0.36 (c=1.0, $CH_2Cl_2$).

Example 6. (3S,4R,5S)-tert-butyl 3,4-dihydroxy-5-(10H-phenoxazin-10-yl)piperidine-1-carboxylate

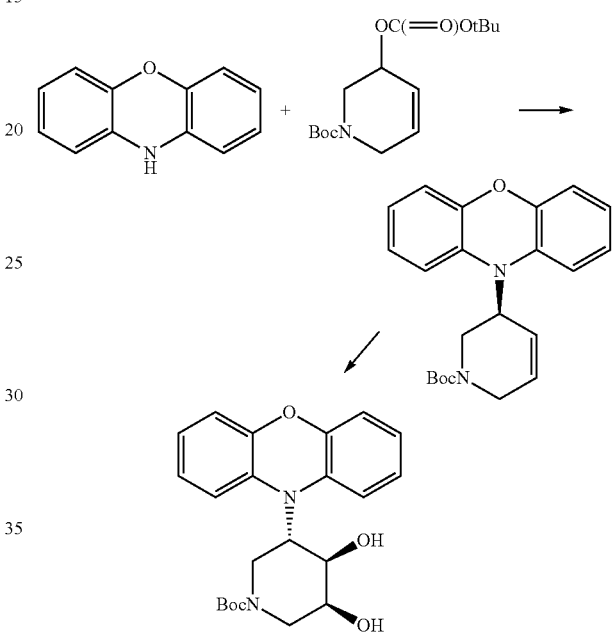

Example 6

To a solution of tert-butyl 5-hydroxy-5,6-dihydropyridine-1(2H)-carboxylate (0.500 g, 2.50 mmol) in THF (8.0 mL) was added n-butyllithium (2.5 M in hexanes, 0.99 mL, 2.50 mmol) at −78° C. The resulting solution was warmed to 0° C. and stirred for 5 min prior to addition of di-tert-butyl dicarbonate (0.600 g, 2.76 mmol) in THF (4.0 mL). The reaction was warmed to RT, stirred for 17 h. The reaction was then quenched with water, extracted with ethyl acetate, washed with brine, concentrated, and the residue purified by flash chromatography ($SiO_2$, 0%-3% ethyl acetate-hexanes) to afford crude tert-butyl 5-((tert-butoxycarbonyl)oxy)-5,6-dihydropyridine-1(2H)-carboxylate (0.825 g) as a colorless oil which was taken to the next step without further purification.

A 5 mL Biotage® microwave reaction vial was charged with $Pd_2.dba_3 \cdot CHCl_3$ (0.025 g, 0.024 mmol), and (R,R)-DACH-phenyl Trost ligand (0.052 g, 0.075 mmol). The vial was sealed, evacuated and backfilled with argon three times. Dry degassed dichloromethane (1.25 mL) was added to this vial, and the mixture was stirred at room temperature for 30 min. Racemic tert-butyl cyclohex-2-en-1-yl carbonate (0.359 g, 1.20 mmol) was added to the vial and the contents were transferred to a separate 5 mL Biotage® microwave reaction vial containing 10H-phenoxazine (0.092 g, 0.50 mmol) in dry degassed dichloromethane (1.50 mL). The reaction mixture was stirred at room temperature for 10 days. At this point, the reaction mixture was evaporated onto silica gel and subjected to column chromatography (SiO$_2$; 0%-5% ethylacetate in hexanes) to afford crude (R)-tert-butyl 5-(10H-phenoxazin-10-yl)-5,6-dihydropyridine-1 (2H)-carboxylate (0.141 g) which was taken to the next step without purification.

A solution of (R)-tert-butyl 5-(10H-phenoxazin-10-yl)-5, 6-dihydropyridine-1(2H)-carboxylate (0.126 g, 0.346 mmol), 4-methylmorpholine N-oxide monohydrate (0.089 g, 0.761 mmol), and osmium tetroxide (0.080 mL, 0.007 mmol, 2.5% in tert-butanol) in tert-butanol (2.0 mL) and water (0.40 mL), was stirred at RT for 42 h. The reaction mixture was treated with solid sodium bisulfite solution, stirred for 1 h, evaporated on to silica and purified by flash chromatography (SiO$_2$, 0%-70% ethyl acetate-hexanes) to afford (R)-tert-butyl 5-(10H-phenoxazin-10-yl)-5,6-dihydropyridine-1(2H)-carboxylate (Example 6) (0.091 g, 51% over two steps from phenoxazine). $^1$H NMR (600 MHz, MeOD) δ 7.02 (2H, bs), 6.91 (2H, bs), 6.83-6.76 (4H, bs), 4.34-4.12 (3H, m), 4.00-3.97 (2H, m), 3.19-3.15 (1H, m), 3.06-2.93 (1H, m), 1.46 (9H, bs); $^{13}$C NMR (150 MHz, MeOD) δ 147.5, 134.1, 128.1, 123.4, 121.8, 115.5, 114.8, 80.5, 53.8, 43.4, 42.7, 42.0, 40.7, 27.4; LCMS m/z 399.1909 ([M+H$^+$], C$_{22}$H$_{27}$N$_2$O$_5$ requires 399.1915). Material produced in this fashion exhibited [α]$_D$=+64.0 (c=0.25, CH$_3$OH). The enantiomeric identity and purity was also confirmed by analytical chiral HPLC >99% (CHIRAL-PAK® IF-3 column, 90:10:0.1 hexanes-EtOH-diethylamine, 1.0 mL/min, retention time: 8.42 min.

Example 7. (3S,4R,5S)-5-(3,6-difluoro-9H-carbazol-9-yl)tetrahydro-2H-pyran-3,4-diol

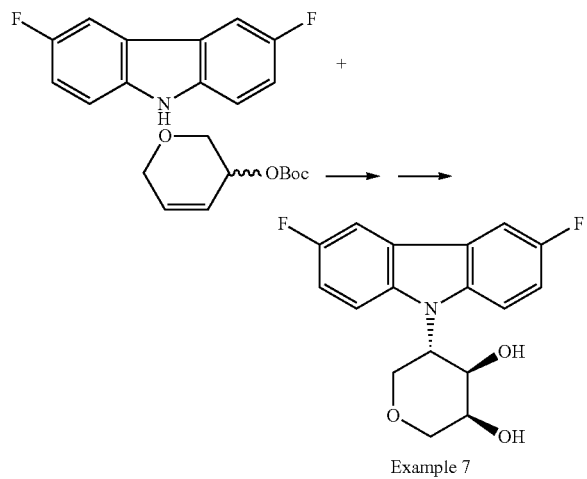

Example 7

A 20 mL Biotage® microwave reaction vial was charged with Pd$_2$.dba$_3$. CHCl$_3$ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 3,6-difluoro-9H-carbazole (0.406 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO$_2$; 0%-5% ethylacetate in hexanes) (0.251 g), which was taken to the next step without further purification.

A solution of (R)-9-(3,6-dihydro-2H-pyran-3-yl)-3,6-difluoro-9H-carbazole (0.251 g, 0.879 mmol), 4-methylmorpholine N-oxide monohydrate (0.226 g, 1.93 mmol), and osmium tetroxide (0.160 mL, 0.017 mmol, 2.5% in tert-butanol) in tert-butanol (1.00 mL) and water (0.20 mL), was stirred at RT for 36 h. The reaction mixture was treated with solid sodium bisulfite, stirred for 1 h, evaporated on to silica, and purified by flash chromatography (SiO$_2$, 0%-70% ethyl acetate-hexanes) to afford (3S,4R,5S)-5-(3,6-difluoro-9H-carbazol-9-yl)tetrahydro-2H-pyran-3,4-diol (Example 7) (0.250 g, 39% over two steps). $^1$H NMR (600 MHz, CDCl$_3$) δ 7.69 (2H, d, J=6.6 Hz), 7.46 (2H, dd, J=9.0, 3.6 Hz), 7.22 (2H, bs), 4.95 (1H, td, J=10.8, 5.4 Hz), 4.70 (1H, dd, J=10.2, 3.0 Hz), 4.26-4.17 (3H, m), 4.09 (1H, dd, J=11.4, 5.4 Hz), 3.78 (1H, d, J=13.2 Hz), 2.63 (1H, bs), 2.16 (1H, bs); LCMS m/z 320.1075 ([M+H$^+$], C$_{17}$H$_{16}$F$_2$NO$_3$ requires 320.1093). Material produced in this fashion exhibited [α]$_D$=−36.0° (c=0.25, CH$_3$OH).

Example 8. (3S,4R,5S)-5-(3-fluoro-9H-carbazol-9-yl)tetrahydro-2H-pyran-3,4-diol

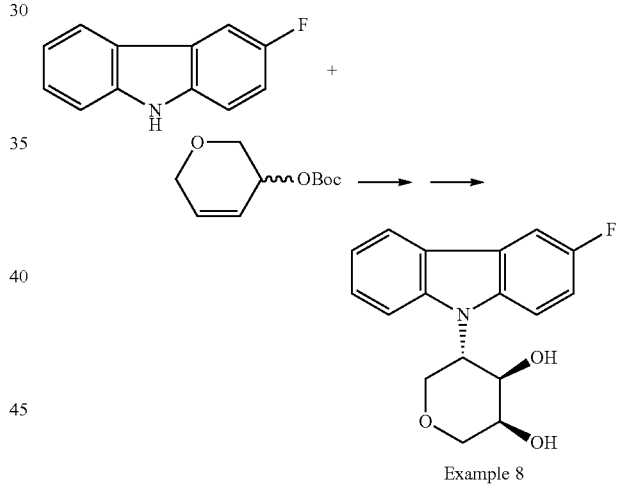

Example 8

A 20 mL Biotage® microwave reaction vial was charged with Pd$_2$.dba$_3$. CHCl$_3$ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 3-fluoro-9H-carbazole (0.370 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO$_2$; 0%-5% ethylacetate in hexanes) to afford slightly crude (R)-9-(3,6-dihydro-2H-pyran-3-yl)-3-fluoro-9H-carbazole (0.403 g), which was taken to the next step without further purification.

A solution of (R)-9-(3,6-dihydro-2H-pyran-3-yl)-3-fluoro-9H-carbazole (0.403 g, 1.50 mmol), 4-methylmorpholine N-oxide monohydrate (0.386 g, 3.30 mmol), and osmium tetroxide (0.320 mL, 0.030 mmol, 2.5% in tert-butanol) in tert-butanol (2.00 mL) and water (0.40 mL), was stirred at RT for 36 h. The reaction mixture was treated with solid sodium bisulfite, stirred for 1 h, evaporated on to silica, and purified by flash chromatography (SiO$_2$, 0%-70% ethyl acetate-hexanes) to afford (3S,4R,5S)-5-(3-fluoro-9H-carbazol-9-yl)tetrahydro-2H-pyran-3,4-diol (Example 8) (0.339 g, 68% over two steps). $^1$H NMR (600 MHz, CDCl$_3$) δ 8.04 (1H, d, J=6.6 Hz), 7.75 (1H, d, J=6.0 Hz), 7.53-7.43 (3H, m), 7.25 (1H, t, J=6.6 Hz), 7.19 (1H, bs), 4.98 (1H, bs), 4.72 (1H, bs), 4.24-4.18 (3H, m), 4.07 (1H, dd, J=11.4, 5.4 Hz), 3.76 (1H, d, J=13.2 Hz), 2.69 (1H, bs), 2.21 (1H, bs); LCMS m/z 302.1180 ([M+H$^+$], C$_{17}$H$_{17}$FNO$_3$ requires 302.1187). Material produced in this fashion exhibited [α]$_D$=–32.0° (c=0.25, CH$_3$OH).

Example 9. (3S,4R,5S)-5-(3,6-dichloro-9H-carbazol-9-yl)tetrahydro-2H-pyran-3,4-diol

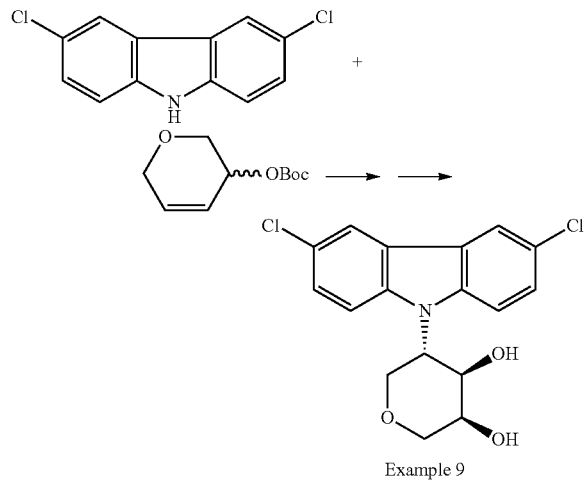

Example 9

A 20 mL Biotage® microwave reaction vial was charged with Pd$_2$.dba$_3$.CHCl$_3$ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 3,6-dichloro-9H-carbazole (0.472 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO$_2$; 0%-5% ethylacetate in hexanes) to afford slightly crude (R)-3,6-dichloro-9-(3,6-dihydro-2H-pyran-3-yl)-9H-carbazole (0.582 g) which was taken to the next step without further purification.

A solution of (R)-3,6-dichloro-9-(3,6-dihydro-2H-pyran-3-yl)-9H-carbazole (0.582 g, 1.80 mmol), 4-methylmorpholine N-oxide monohydrate (0.464 g, 3.96 mmol), and osmium tetroxide (0.370 mL, 0.036 mmol, 2.5% in tert-butanol) in tert-butanol (3.00 mL) and water (0.60 mL), was stirred at RT for 36 h. The reaction mixture was treated with solid sodium bisulfite, stirred for 1 h, evaporated on to silica, and purified by flash chromatography (SiO$_2$, 0%-70% ethyl acetate-hexanes) to afford (3S,4R,5S)-5-(3,6-dichloro-9H-carbazol-9-yl)tetrahydro-2H-pyran-3,4-diol (Example 9) (0.488 g, 69% over two steps). $^1$H NMR (600 MHz, DMSO-d$^6$) δ 8.33 (2H, bs), 7.78 (2H, bs), 7.45 (2H, bs), 4.93 (1H, d, J=4.8 Hz), 4.90-4.85 (2H, m), 4.54-4.50 (1H, m), 4.11 (1H, t, J=10.8 Hz), 3.87-3.83 (4H, m); $^{13}$C NMR (150 MHz, DMSO-d$^6$) δ 126.6, 124.2, 120.9, 71.4, 69.7, 68.3, 66.6, 54.9; LCMS m/z 352.0483 ([M+H$^+$], C$_{17}$H$_{16}$Cl$_2$NO$_3$ requires 352.0502). Material produced in this fashion exhibited [α]D=–12.0° (c=0.25, CH$_3$OH).

Other 1-amino-2,3-diols may be synthesized in analogous fashion as shown in Examples 10-15

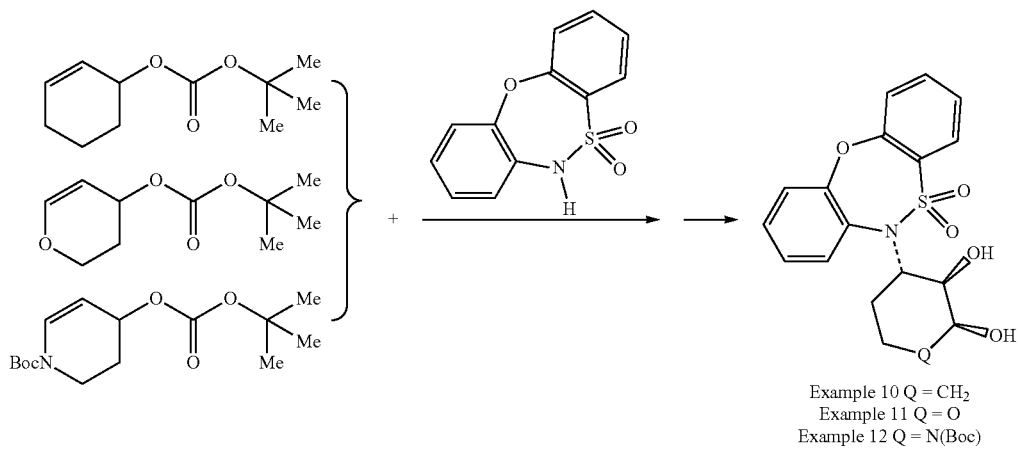

Example 10 Q = CH$_2$
Example 11 Q = O
Example 12 Q = N(Boc)

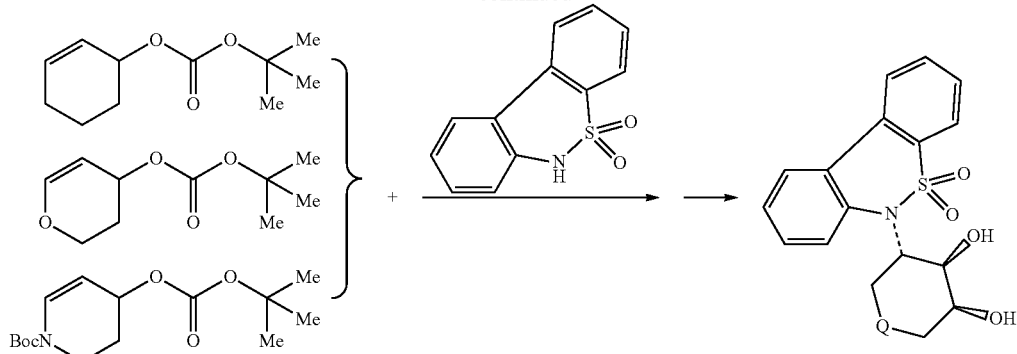

Example 13 Q = CH₂
Example 14 Q = O
Example 15 Q = N(Boc)

Example 16. (3S,4R,5S)-5-(2-fluoro-10H-phenoxazin-10-yl)tetrahydro-2H-pyran-3,4-diol

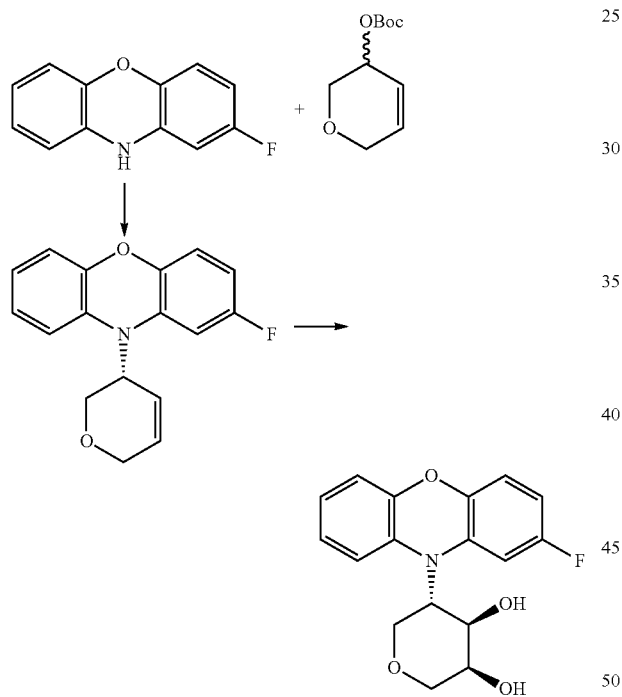

A 20 mL Biotage® microwave reaction vial was charged with Pd₂.dba₃. CHCl₃ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 2-fluoro-10H-phenoxazine (0.402 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO₂; 0%-5% ethylacetate in hexanes) to afford slightly crude (R)-10-(3,6-dihydro-2H-pyran-3-yl)-2-fluoro-10H-phenoxazine (0.650 g), which was taken to the next step without further purification.

A solution of (R)-10-(3,6-dihydro-2H-pyran-3-yl)-2-fluoro-10H-phenoxazine (0.650 g, 2.29 mmol), 4-methylmorpholine N-oxide monohydrate (0.591 g, 5.05 mmol), and osmium tetroxide (0.466 mL, 0.045 mmol, 2.5% in tert-butanol) in tert-butanol (3.00 mL) and water (0.60 mL), was stirred at RT for 36 h. The reaction mixture was treated with solid sodium bisulfite, stirred for 1 h, evaporated on to silica, and purified by flash chromatography (SiO₂, 0%-70% ethyl acetate-hexanes) to afford title compound (0.557 g, 89% over two steps). ¹H NMR (600 MHz, MeOD) δ 6.99 (1H, dd, J=7.8, 0.6 Hz), 6.92-6.89 (1H, m), 6.83 (1H, td, J=7.8, 1.2 Hz), 6.77 (1H, dd, J=10.2, 3.0 Hz), 6.74 (1H, dd, J=7.8, 1.2 Hz), 6.71 (1H, dd, J=8.4, 5.4 Hz), 6.52 (1H, td, J=8.4, 2.4 Hz), 4.29 (1H, dd, J=10.2, 3.0 Hz), 4.10-4.06 (2H, m), 3.95 (1H, bs), 3.90 (1H, d, J=14.4 Hz), 3.81-3.77 (1H, m), 3.61 (1H, d, J=12.6 Hz); ¹³C NMR (150 MHz, MeOD) δ 160.0, 158.4, 149.1, 145.2, 137.0, 134.1, 132.6, 129.4, 128.2, 123.5, 122.9, 117.9, 115.8, 115.7, 107.8, 107.6, 105.0, 104.8, 71.0, 70.2, 68.5, 68.1, 61.9; HRMS m/z 318.1135 ([M+H⁺], C₁₇H₁₇FNO₄ requires 318.1136). Material produced in this fashion exhibited [α]_D=+38.0° (c=1.0, CH₃OH).

Example 17. (3S,4R,5S)-5-(2-(trifluoromethyl)-10H-phenoxazin-10-yl)tetrahydro-2H-pyran-3,4-diol

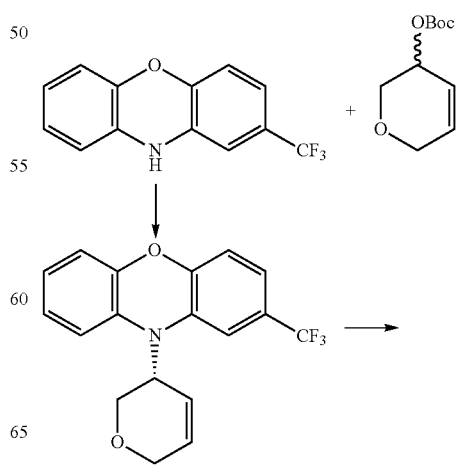

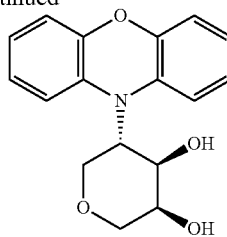
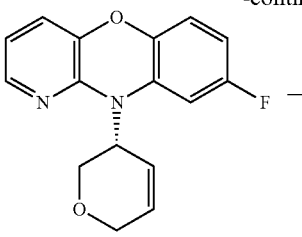

A 20 mL Biotage® microwave reaction vial was charged with Pd$_2$.dba$_3$. CHCl$_3$ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 2-(trifluoromethyl)-10H-phenoxazine (0.502 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO$_2$; 0%-5% ethylacetate in hexanes) to afford slightly crude (R)-10-(3,6-dihydro-2H-pyran-3-yl)-2-(trifluoromethyl)-10H-phenoxazine (0.678 g), which was taken to the next step without further purification.

A solution of (R)-10-(3,6-dihydro-2H-pyran-3-yl)-2-(trifluoromethyl)-10H-phenoxazine (0.678 g, 2.03 mmol), 4-methylmorpholine N-oxide monohydrate (0.525 g, 4.48 mmol), and osmium tetroxide (0.413 mL, 0.041 mmol, 2.5% in tert-butanol) in tert-butanol (3.00 mL) and water (0.60 mL), was stirred at RT for 36 h. The reaction mixture was treated with solid sodium bisulfite, stirred for 1 h, evaporated on to silica, and purified by flash chromatography (SiO$_2$, 0%-70% ethyl acetate-hexanes) to afford title compound (0.654 g, 89% over two steps). $^1$H NMR (600 MHz, CDCl$_3$) δ 7.15 (1H, bs), 7.08 (1H, d, J=7.8 Hz), 6.97 (1H, dd, J=8.4, 1.2 Hz), 6.92 (1H, td, J=7.2, 1.2 Hz), 6.85-6.81 (2H, m), 6.75 (1H, dd, J=7.8, 1.2 Hz), 4.21 (1H, dd, J=10.2, 3.0 Hz), 4.10-4.05 (2H, m), 3.93-3.89 (2H, m), 3.76-3.72 (1H, m), 3.55 (1H, d, J=12.6 Hz); $^{13}$C NMR (150 MHz, MeOD) δ 151.9, 148.6, 136.8, 133.8, 125.9, 125.7, 125.5, 125.3, 125.2, 124.0, 123.2, 119.7, 118.4, 115.9, 115.8, 114.4, 71.1, 70.1, 68.54, 68.53, 62.6; LCMS m/z 368.1100 ([M+H]$^+$, C$_{18}$H$_{17}$F$_3$NO$_4$ requires 368.1104). Material produced in this fashion exhibited [α]$_D$=+31.0° (c=1.0, CH$_3$OH).

Example 18. (3S,4R,5S)-5-(8-fluoro-10H-benzo[b]pyrido[2,3-e][1,4]oxazin-10-yl)tetrahydro-2H-pyran-3,4-diol

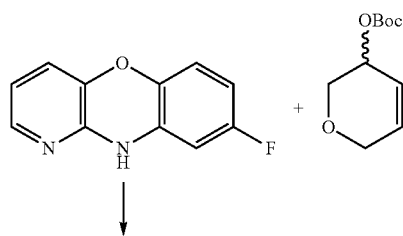

A 20 mL Biotage® microwave reaction vial was charged with Pd$_2$.dba$_3$. CHCl$_3$ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 8-fluoro-10H-benzo[b]pyrido[2,3-e][1,4]oxazine (0.404 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO$_2$; 0%-5% ethylacetate in hexanes) to afford slightly crude (R)-10-(3,6-dihydro-2H-pyran-3-yl)-8-fluoro-10H-benzo[b]pyrido[2,3-e][1,4]oxazine (0.568 g) which was taken to the next step without further purification.

A solution of (R)-10-(3,6-dihydro-2H-pyran-3-yl)-8-fluoro-10H-benzo[b]pyrido[2,3-e][1,4]oxazine (0.568 g, 1.99 mmol), 4-methylmorpholine N-oxide monohydrate (0.568 g, 1.99 mmol), and osmium tetroxide (0.413 mL, 0.039 mmol, 2.5% in tert-butanol) in tert-butanol (3.00 mL) and water (0.60 mL), was stirred at RT for 36 h. The reaction mixture was treated with solid sodium bisulfite, stirred for 1 h, evaporated on to silica, and purified by flash chromatography (SiO$_2$, 0%-70% ethyl acetate-hexanes) to afford to afford title compound (0.540 g, 84% over two steps). $^1$H NMR (600 MHz, MeOD) δ 7.68-7.67 (1H, m), 6.91-6.90 (1H, m), 6.83 (1H, dd, J=10.8, 2.4 Hz), 6.702-6.66 (2H, m), 6.46 (1H, td, J=8.4, 2.4 Hz), 5.03 (1H, dd, J=10.2, 2.4 Hz), 4.39 (1H, t, J=10.8 Hz), 4.30 (1H, td, J=10.2, 3.6 Hz), 3.96-3.88 (3H, m), 3.64 (1H, d, J=12.0 Hz); $^{13}$C NMR (150 MHz, MeOD) δ 160.57, 158.9, 146.2, 142.1, 141.8, 140.7, 136.4, 121.0, 117.6, 115.8, 115.7, 107.0, 106.1, 101.9, 101.7, 71.3, 70.3, 67.6, 66.5, 56.5; LCMS m/z 319.1091 ([M+H]$^+$, C$_{16}$H$_{16}$FN$_2$O$_4$ requires 319.1089). Material produced in this fashion exhibited [α]$_D$=+53.0° (c=1.0, CH$_3$OH).

Example 19. (3S,4R,5S)-5-(9H-carbazol-9-yl)tetrahydro-2H-pyran-3,4-diol

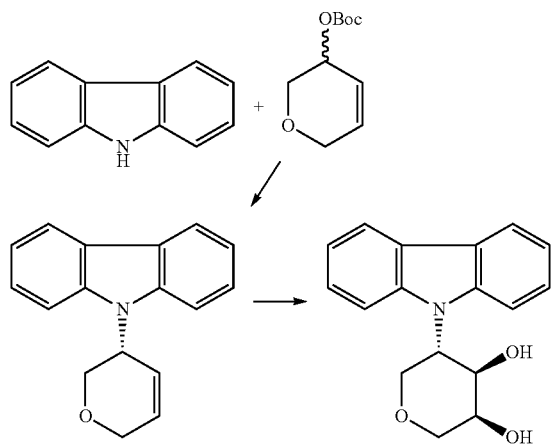

A 20 mL Biotage® microwave reaction vial was charged with Pd₂.dba₃. CHCl₃ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 9H-carbazole (0.334 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO₂; 0%-5% ethylacetate in hexanes) to afford slightly crude (R)-9-(3,6-dihydro-2H-pyran-3-yl)-9H-carbazole (0.234 g), which was taken to the next step without further purification.

A solution of (R)-9-(3,6-dihydro-2H-pyran-3-yl)-9H-carbazole (0.234 g, 0.939 mmol), 4-methylmorpholine N-oxide monohydrate (0.241 g, 2.06 mmol), and osmium tetroxide (0.200 mL, 0.018 mmol, 2.5% in tert-butanol) in tert-butanol (2.00 mL) and water (0.40 mL), was stirred at RT for 36 h. The reaction mixture was treated with solid sodium bisulfite, stirred for 1 h, evaporated on to silica, and purified by flash chromatography (SiO₂, 0%-70% ethyl acetate-hexanes) to afford (3S,4R,5S)-5-(9H-carbazol-9-yl)tetrahydro-2H-pyran-3,4-diol (0.129 g, 23% over two steps). $^1$H NMR (600 MHz, MeOD) δ 8.06 (2H, d, J=7.8 Hz), 7.66 (2H, bs), 7.41 (2H, t, J=7.8 Hz), 7.18 (2H, t, J=7.8 Hz), 5.06 (1H, td, J=11.4, 5.4 Hz), 4.76 (1H, dd, J=10.8, 3.0 Hz), 4.23 (1H, t, J=11.4 Hz), 4.04-4.02 (2H, m), 3.90 (1H, dd, J=10.8, 4.8 Hz), 3.81 (1H, d, J=11.4 Hz); $^{13}$C NMR (150 MHz, MeOD) δ 125.4, 123.3, 119.8, 118.8, 111.2, 109.3, 71.1, 69.7, 68.4, 66.8, 54.1; LCMS m/z 284.1283 ([M+H⁺], $C_{17}H_{18}NO_3$ requires 284.1282). Material produced in this fashion exhibited [α]$_D$=+9.0° (c=1.0, CH₃OH). The enantiomeric identity and purity was also confirmed by analytical chiral HPLC >99% (CHIRALPAK® IA column, 70:30:0.1 hexanes-EtOH-diethylamine, 1.0 mL/min, retention time: 7.16 min.

Example 20. (3S,4R,5S)-5-(3,6-dimethyl-9H-carbazol-9-yl)tetrahydro-2H-pyran-3,4-diol

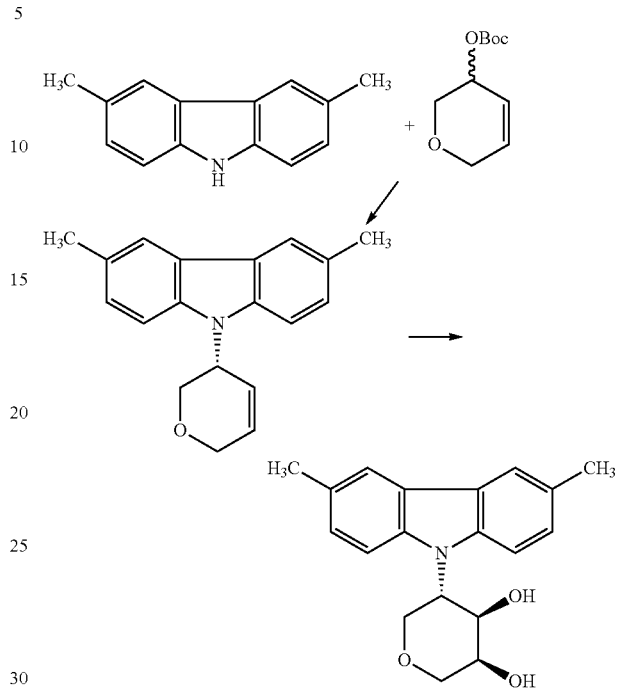

A 20 mL Biotage® microwave reaction vial was charged with Pd₂.dba₃. CHCl₃ (0.103 g, 0.100 mmol), and (R,R)-DACH-phenyl Trost ligand (0.207 g, 0.300 mmol). The vial was sealed, evacuated and backfilled with argon three times. Dry degassed dichloromethane (6.0 mL) was added to this vial, and the mixture was stirred at room temperature for 30 min. Racemic tert-butyl (3,6-dihydro-2H-pyran-3-yl) carbonate (0.960 g, 4.80 mmol) was added to the vial and the contents were transferred to a separate 20 mL Biotage® microwave reaction vial containing 3,6-dimethyl-9H-carbazole (0.390 g, 2.00 mmol) in dry degassed dichloromethane (5.0 mL). The reaction mixture was stirred at room temperature for 10 days. At this point, the reaction mixture was evaporated onto silica gel and subjected to column chromatography (SiO₂; 0%-5% ethylacetate in hexanes) to afford slightly crude (R)-9-(3,6-dihydro-2H-pyran-3-yl)-3,6-dimethyl-9H-carbazole (0.347 g), which was taken to the next step without further purification.

A solution of (R)-3,6-dichloro-9-(3,6-dihydro-2H-pyran-3-yl)-9H-carbazole (0.347 g, 1.25 mmol), 4-methylmorpholine N-oxide monohydrate (0.322 g, 2.75 mmol), and osmium tetroxide (0.320 mL, 0.025 mmol, 2.5% in tert-butanol) in tert-butanol (2.00 mL) and water (0.40 mL), was stirred at RT for 36 h. The reaction mixture was treated with solid sodium bisulfite, stirred for 1 h, evaporated on to silica, and purified by flash chromatography (SiO₂, 0%-70% ethyl acetate-hexanes) to afford (3S,4R,5S)-5-(3,6-dimethyl-9H-carbazol-9-yl)tetrahydro-2H-pyran-3,4-diol (0.157 g, 25% over two steps). $^1$H NMR (600 MHz, MeOD) δ 7.80 (2H, bs), 7.44 (2H, bs), 7.18 (2H, bs), 4.93-4.88 (1H, m), 4.60 (1H, bs), 4.06-3.92 (3H, m), 3.78 (1H, bs), 3.65-3.63 (1H, m), 2.45 (6H, s); $^{13}$C NMR (150 MHz, MeOD) δ 127.9, 126.6, 123.5, 119.7, 110.3, 109.1, 71.1, 69.6, 68.5, 66.8, 54.1, 20.3; LCMS m/z 312.1604 ([M+H⁺], $C_{19}H_{22}NO_3$ requires 312.1595). Material produced in this fashion exhib-

Example 21: (3S,4R,5S)-tert-butyl 3-(3,6-difluoro-9H-carbazol-9-yl)-4,5-dihydroxypiperidine-1-carboxylate

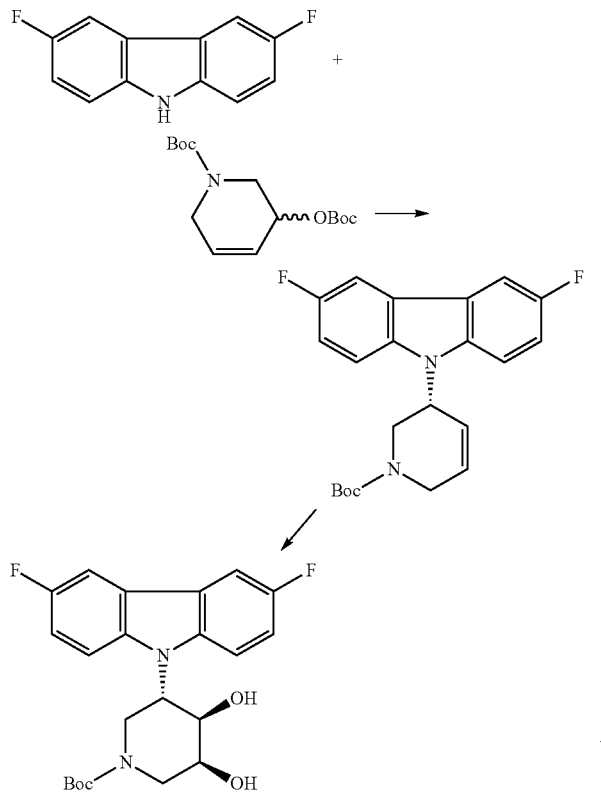

Example 22 (3S,4R,5S)-tert-butyl 3-(3,7-bis(trifluoromethyl)-10H-phenoxazin-10-yl)-4,5-dihydroxypiperidine-1-carboxylate

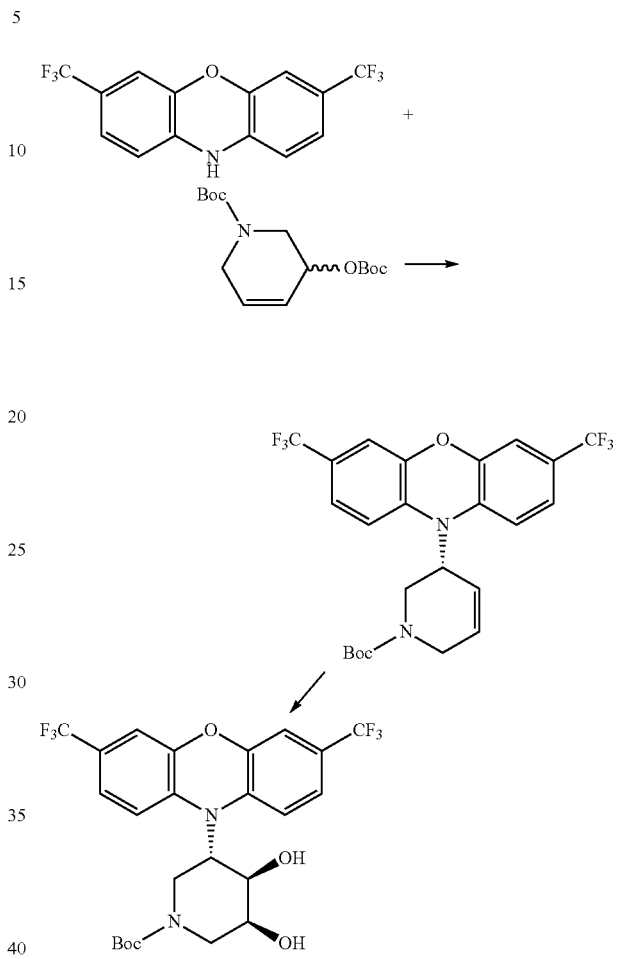

Using the typical procedure 3,6-difluoro-9H-carbazole (0.609 g, 3.00 mmol) was reacted with tert-butyl 5-((tert-butoxycarbonyl)oxy)-5,6-dihydropyridine-1(2H)-carboxylate (2.15 g, 7.20 mmol) in presence of (R,R)-L1 for 10 days to afford crude (R)-tert-butyl 5-(3,6-difluoro-9H-carbazol-9-yl)-5,6-dihydropyridine-1(2H)-carboxylate (1.33 g) which was taken to the next step without further purification.

Using the typical procedure (R)-tert-butyl 5-(3,6-difluoro-9H-carbazol-9-yl)-5,6-dihydropyridine-1(2H)-carboxylate (0.666 g, 1.73 mmol) was transformed to (3S,4R,5S)-tert-butyl 3-(3,6-difluoro-9H-carbazol-9-yl)-4,5-dihydroxypiperidine-1-carboxylate (0.409 g, 65% over two steps). $^1$H NMR (600 MHz, MeOD) δ reported as a mixture of rotamers δ 7.78-7.72 (3H, m), 7.57 (1H, br s), 7.20 (2H, br s), 4.65-4.61 (1H, m), 4.28 (1H, br s), 4.17-4.09 (2H, m), 3.78-3.50 (2H, m), 3.30-3.20 (2H, m), 9H [1.49 (br s); 1.45 (br s)]; Material produced in this fashion exhibited $[\alpha]^{25}_D$=+17.0° (c=1.0, CH$_3$OH). HPLC analysis: >99% ee (CHIRALPAK IA-3, 80:20:0.1 hexanes-EtOH-diethylamine, 1.0 mL/min, UV: 254 nm), tR=1.64 min; HRMS m/z 363.1157 ([M+H$^+$–t-Bu], C$_{18}$H$_{17}$F$_2$N$_2$O$_4$ requires 363.1151).

Using the typical procedure 3,7-bis(trifluoromethyl)-10H-phenoxazine (0.957 g, 3.00 mmol) was reacted with tert-butyl 5-((tert-butoxycarbonyl)oxy)-5,6-dihydropyridine-1(2H)-carboxylate (2.15 g, 7.20 mmol) in presence of (R,R)-L1 for 10 days to afford crude (R)-tert-butyl 5-(3,7-bis(trifluoromethyl)-10H-phenoxazin-10-yl)-5,6-dihydropyridine-1(2H)-carboxylate (1.45 g) which was taken to the next step without further purification.

Using the typical procedure (R)-tert-butyl 5-(3,7-bis(trifluoromethyl)-10H-phenoxazin-10-yl)-5,6-dihydropyridine-1(2H)-carboxylate (0.725 g, 1.44 mmol) was transformed to (3S,4R,5S)-tert-butyl 3-(3,7-bis(trifluoromethyl)-10H-phenoxazin-10-yl)-4,5-dihydroxypiperidine-1-carboxylate (0.623 g, 78% over two steps). $^1$H NMR (600 MHz, MeOD) δ reported as a mixture of rotamers δ 7.23-7.21 (2H, m), 7.18-7.12 (2H, m), 7.02 (2H, br s), 4.36 (2H, dd, J=10.8, 3.0 Hz), 2H [4.23-4.17 (m); 4.14-4.10 (m)], 4.02-3.99 (1H, m), 3.48-3.44 (1H, m), 1H [3.15 (d, J=13.8 Hz); 3.05 (d, J=13.8 Hz)], 1.50 (9H, br s); Material produced in this fashion exhibited $[\alpha]^{25}_D$=+51.0° (c=0.25, CH$_3$OH). HPLC analysis: >99% ee (CHIRALPAK IF-3, 90:10:0.1 hexanes-EtOH-diethylamine, 1.0 mL/min, UV: 254 nm), tR=3.87 min; HRMS m/z 479.1047 ([M+H$^+$-t-Bu], C$_{20}$H$_{17}$F$_6$N$_2$O$_5$ requires 479.1037).

Example 23 (3S,4R,5S)-tert-butyl 3-(3,6-dichloro-9H-carbazol-9-yl)-4,5-dihydroxypiperidine-1-carboxylate

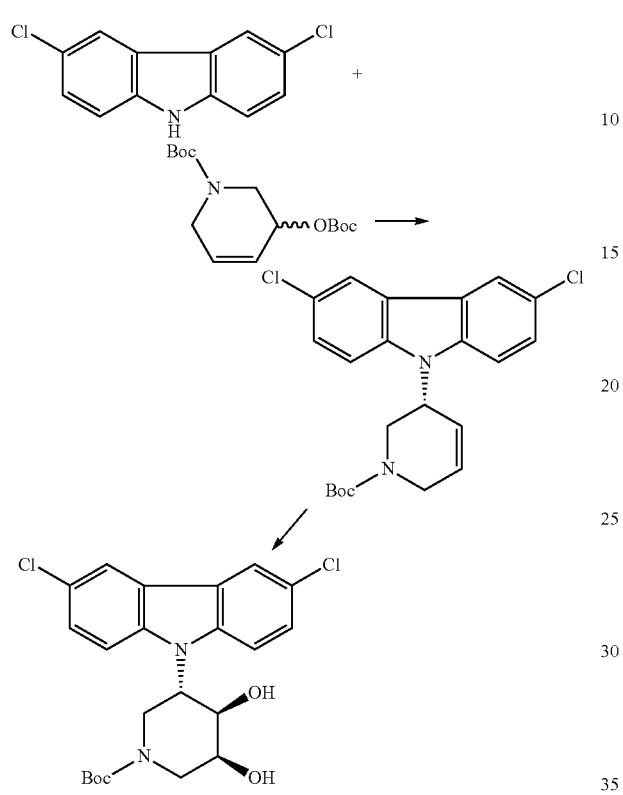

Using the typical procedure 3,6-dichloro-9H-carbazole (0.708 g, 3.00 mmol) was reacted with tert-butyl 5-((tert-butoxycarbonyl)oxy)-5,6-dihydropyridine-1(2H)-carboxylate (2.15 g, 7.20 mmol) in presence of (R,R)-L1 for 10 days to afford crude (R)-tert-butyl 5-(3,6-dichloro-9H-carbazol-9-yl)-5,6-dihydropyridine-1(2H)-carboxylate (1.28 g) which was taken to the next step without further purification.

Using the typical procedure (R)-tert-butyl 5-(3,6-dichloro-9H-carbazol-9-yl)-5,6-dihydropyridine-1(2H)-carboxylate (0.644 g, 1.44 mmol) was transformed to (3S,4R,5S)-tert-butyl 3-(3,6-dichloro-9H-carbazol-9-yl)-4,5-dihydroxypiperidine-1-carboxylate (0.646 g, 95% over two steps). $^1$H NMR (600 MHz, MeOD) δ reported as a mixture of rotamers δ 8.10 (2H, br s), 7.74-7.58 (2H, br s), 7.41 (2H, br s), 4.64-4.63 (1H, m), 4.29 (1H, br s), 4.18-4.08 (3H, m), 3.77-3.52 (1H, m), 3.28-3.21 (1H, m), 9H [1.50 (br s); 1.45 (br s)]; Material produced in this fashion exhibited $[\alpha]^{25}$D=+24.0° (c=1.0, CH$_3$OH). HPLC analysis: >99% ee (CHIRALPAK IA-3, 80:20:0.1 hexanes-EtOH-diethylamine, 1.0 mL/min, UV: 254 nm), tR=1.83 min; LCMS m/z 395.0596 ([M+H$^+$-t-Bu], C$_{18}$H$_{17}$C$_{12}$N$_2$O$_4$ requires 395.0560).

Example 24 (1S,2R,3S)-3-(10H-phenoxazin-10-yl)cyclopentane-1,2-diol

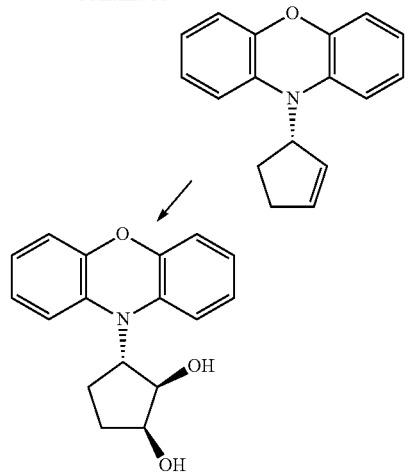

Using the typical procedure 10H-phenoxazine (0.366 g, 2.00 mmol) was reacted with tert-butyl cyclopent-2-en-1-yl carbonate (0.884 g, 4.80 mmol) in presence of (R,R)-L1 for 10 days to afford (S)-10-(cyclopent-2-en-1-yl)-10H-phenoxazine (0.454 g, 91%). $^1$H NMR (600 MHz, MeOD) δ 6.83-6.77 (4H, m), 6.73-6.69 (4H, m), 6.02-6.00 (1H, m), 5.90-5.89 (1H, m), 5.14-5.11 (1H, m), 2.69-2.65 (1H, m), 2.60-2.54 (1H, m), 2.45-2.39 (1H, m), 2.12-2.06 (1H, m); $^{13}$C NMR (150 MHz, MeOD) δ 147.9, 135.1, 133.0, 132.1, 123.3, 121.1, 115.2, 114.8, 65.4, 31.3, 25.1; LCMS m/z 250.0939 ([M+H$^+$], C$_{17}$H$_{16}$NO requires 250.1227).

Using the typical procedure (S)-10-(cyclopent-2-en-1-yl)-10H-phenoxazine (0.454 g, 1.82 mmol) was transformed to (1S,2R,3S)-3-(10H-phenoxazin-10-yl)cyclopentane-1,2-diol (0.340 g, 66%). $^1$H NMR (600 MHz, MeOD) δ 6.88-6.85 (2H, m), 6.80 (2H, d, J=7.8 Hz), 6.75-6.71 (4H, m), 4.61 (1H, dd, J=9.0, 4.8 Hz), 4.36 (1H, q, J=9.0 Hz), 4.12-4.12 (1H, m), 2.21-2.09 (2H, m), 2.00-1.95 (1H, m), 1.83-1.79 (1H, m); $^{13}$C NMR (150 MHz, MeOD) δ 148.4, 135.3, 123.4, 121.4, 115.4, 115.3, 73.1, 71.9, 64.6, 28.6, 21.7; Material produced in this fashion exhibited $[\alpha]^{25}$D=−29.0° (c=1.0, CH$_3$OH). HPLC analysis: 84% ee (CHIRALPAK IA, 70:30 hexanes-EtOH, 1.0 mL/min, UV: 230 nm), tR=5.82 min (major), 7.59 min (minor); LCMS m/z 284.1846 ([M+H$^+$], C$_{17}$H$_{18}$NO$_3$ requires 284.1282).

Example 25
3-(9H-carbazol-9-yl)cycloheptane-1,2-diol

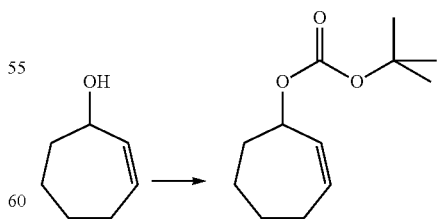

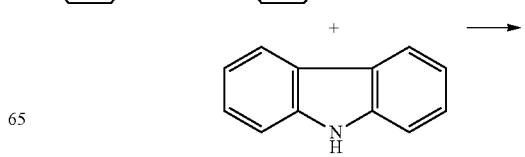

-continued

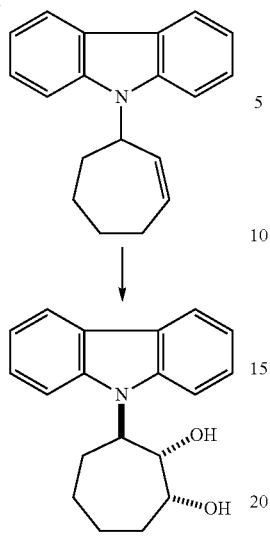

To a solution of cyclohept-2-enol (1.64 g, 14.6 mmol) in THF (49.0 mL) cooled to −78° C., n-butyllithium (6.37 mL, 16.1 mmol, 2.5 M in hexanes) was added. The resulting solution was warmed to 0° C. and stirred for 5 min prior to addition of di-tert-butyl dicarbonate (7.00 g, 32.1 mmol) in THF (25.0 mL). The reaction was warmed to RT, stirred for 16 h. The reaction was then quenched with water, extracted with ethyl acetate, washed with brine, concentrated, and the residue was purified by column chromatography ($SiO_2$, 0%-1% ethyl acetate in hexanes) to give tert-butyl cyclohept-2-en-1-yl carbonate (2.11 g, 68%). $^1$H NMR (600 MHz, MeOD) δ 5.80-5.75 (1H, m), 5.67 (1H, d, J=12.0 Hz), 5.18 (1H, d, J=10.2 Hz), 2.19-2.13 (1H, m), 2.06-2.00 (1H, m), 1.93-1.88 (2H, m), 1.68-1.58 (3H, m), 1.45 (9H, br s), 1.38-1.30 (1H, m); $^{13}$C NMR (150 MHz, MeOD) δ 153.3, 133.9, 131.2, 82.0, 67.0, 33.0, 28.5, 27.9, 26.9, 26.6.

Using the typical procedure, but without chiral palladium catalyst, 9H-carbazole (0.083 g, 0.50 mmol) was reacted with tert-butyl cyclohept-2-en-1-yl carbonate (0.254 g, 1.20 mmol) in presence of triphenylphosphine for 10 days to afford 9-(cyclohept-2-en-1-yl)-9H-carbazole (0.081 g, 63%). $^1$H NMR (600 MHz, MeOD) δ 8.07 (2H, d, J=7.8 Hz), 7.54 (2H, d, J=8.4 Hz), 7.39 (2H, t, J=7.8 Hz), 7.17 (2H, t, J=7.8 Hz), 6.03 (2H, br s), 5.46 (1H, d, J=11.4 Hz), 2.49-2.42 (2H, m), 2.40-2.31 (1H, m), 2.11-2.09 (1H, m), 1.98-1.94 (1H, m), 1.86-1.80 (2H, m), 1.59-1.55 (1H, m); $^{13}$C NMR (150 MHz, MeOD) δ 139.5, 134.1, 131.8, 125.1, 123.2, 119.8, 118.5, 109.8, 56.2, 33.4, 28.9, 28.6, 26.9; LCMS m/z 262.1403 ([M+H$^+$], $C_{19}H_{20}N$ requires 262.1591).

Using the typical procedure 9-(cyclohept-2-en-1-yl)-9H-carbazole (0.081 g, 0.309 mmol) was transformed to rel-(1R,2S,6R)-3-(9H-carbazol-9-yl)cycloheptane-1,2-diol (0.065 g, 71%). $^1$H NMR (600 MHz, MeOD) δ 8.06 (2H, br s), 7.57-7.55 (2H, m), 7.40 (1H, br s), 7.16 (2H, t, J=7.2 Hz), 4.77-4.73 (1H, m), 4.55 (1H, dd, J=8.4, 3.6 Hz), 4.16 (1H, dd, J=8.4, 1.8 Hz), 2.52-2.48 (1H, m), 2.13-2.09 (1H, m), 1.98-1.90 (2H, m), 1.78-1.67 (2H, m), 1.65-1.60 (2H, m); $^{13}$C NMR (150 MHz, MeOD) δ 125.3, 119.9, 119.5, 118.4, 111.0, 109.1, 74.2, 72.7, 60.4, 30.6, 20.5, 28.1, 25.0; HPLC analysis: (CHIRALPAK IF-3, 70:30 hexanes-EtOH, 1.5 mL/min, UV: 254 nm), tR=4.40 min, 7.69 min; LCMS m/z 296.0822 ([M+H$^+$], $C_{19}H_{22}NO_2$ requires 296.1646).

Example 26 (1S,2R,3S)-3-(9H-carbazol-9-yl)cycloheptane-1,2-diol

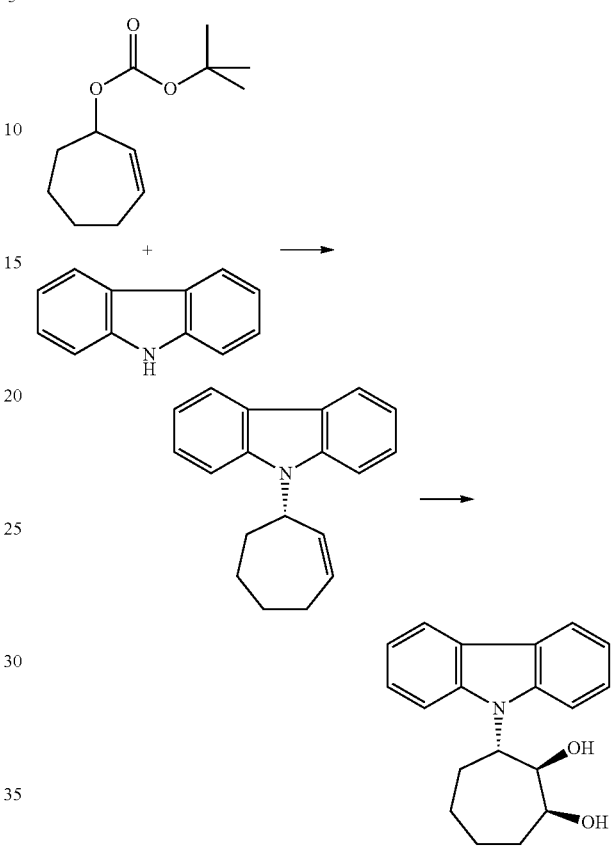

Using the typical procedure 9H-carbazole (0.167 g, 1.00 mmol) was reacted with tert-butyl cyclohept-2-en-1-yl carbonate (0.509 g, 2.40 mmol) in presence of (R,R)-L1 for 10 days to afford (S)-9-(cyclohept-2-en-1-yl)-9H-carbazole (0.011 g, 4%). $^1$H NMR (600 MHz, MeOD) δ 8.07 (2H, d, J=7.8 Hz), 7.54 (2H, d, J=8.4 Hz), 7.39 (2H, t, J=7.8 Hz), 7.17 (2H, t, J=7.8 Hz), 6.03 (2H, br s), 5.46 (1H, d, J=11.4 Hz), 2.49-2.40 (2H, m), 2.36-2.31 (1H, m), 2.11-2.09 (1H, m), 1.98-1.94 (1H, m), 1.86-1.80 (2H, m), 1.59-1.55 (1H, m); $^{13}$C NMR (150 MHz, MeOD) δ 139.5, 134.1, 131.8, 125.1, 123.2, 119.8, 118.5, 109.8, 56.2, 33.4, 28.9, 28.6, 26.9; LCMS m/z 262.2402 ([M+H$^+$], $C_{19}H_{20}N$ requires 262.1591).

Using the typical procedure (S)-9-(cyclohept-2-en-1-yl)-9H-carbazole (0.011 g, 0.042 mmol) was transformed to (1S,2R,3S)-3-(9H-carbazol-9-yl)cycloheptane-1,2-diol (0.008 g, 67%). $^1$H NMR (600 MHz, MeOD) δ 8.06 (2H, br s), 7.569-7.560 (2H, m), 7.40 (2H, br s), 7.16 (2H, t, J=7.2 Hz), 4.76-4.73 (1H, m), 4.55 (1H, dd, J=9.0, 3.6 Hz), 4.16 (1H, dd, J=9.0, 2.4 Hz), 2.52-2.48 (1H, m), 2.13-2.09 (1H, m), 1.98-1.90 (2H, m), 1.78-1.60 (4H, m); $^{13}$C NMR (150 MHz, MeOD) δ 125.2, 119.8, 119.5, 118.4, 111.0, 109.1, 74.2, 72.7, 60.4, 30.6, 30.5, 28.1, 25.0; HPLC analysis: 49% ee (CHIRALPAK IF-3, 70:30 hexanes-EtOH, 1.5 mL/min, UV: 254 nm), tR=4.47 min (minor), 7.86 min (major); LCMS m/z 296.0822 ([M+H$^+$], $C_{19}H_{22}NO_2$ requires 296.1646).

Example 27 (1S,2R,3S)-3-(10H-phenoxazin-10-yl)cycloheptane-1,2-diol

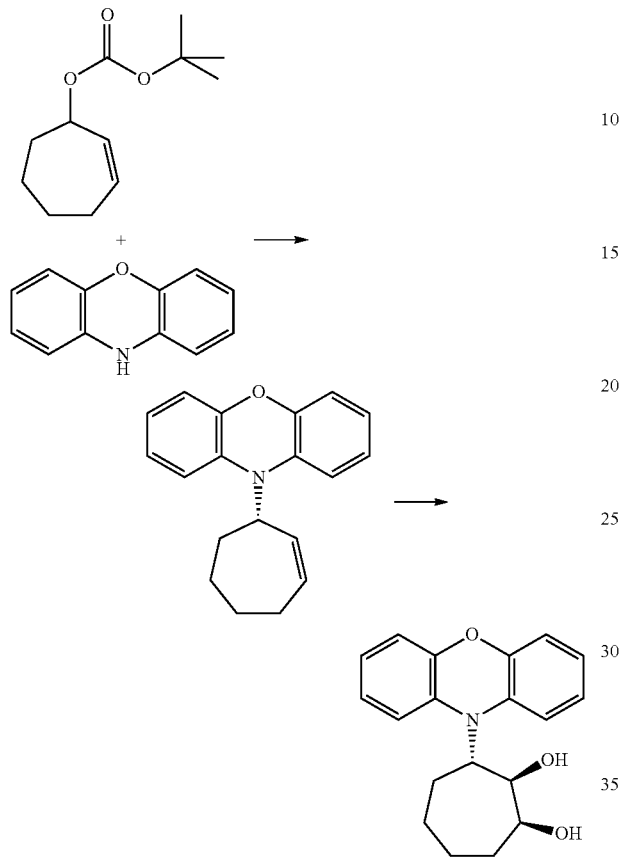

Example 28 (3R,4S,5R)-tert-butyl 5-(9H-carbazol-9-yl)-3,4-dihydroxypiperidine-1-carboxylate

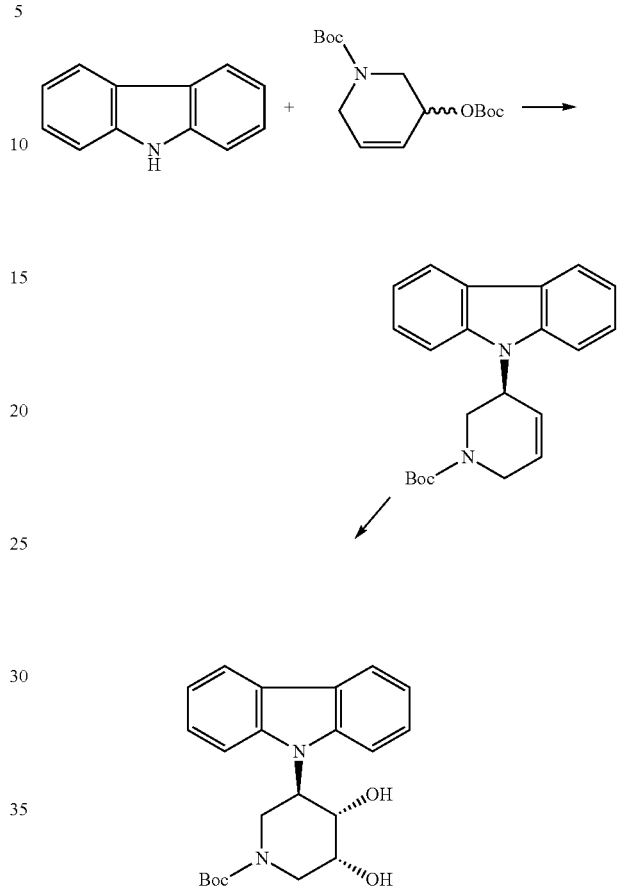

Using the typical procedure 10H-phenoxazine (0.366 g, 2.00 mmol) was reacted with tert-butyl cyclohept-2-en-1-yl carbonate (1.02 g, 4.80 mmol) in presence of (R,R)-L1 for 10 days to afford (S)-10-(cyclohept-2-en-1-yl)-10H-phenoxazine (0.473 g, 85%). $^1$H NMR (600 MHz, MeOD) δ 6.85-6.83 (2H, m), 6.73-6.70 (6H, m), 5.96-5.90 (2H, m), 4.61 (1H, d, J=10.8 Hz), 2.40-2.36 (1H, m), 2.30-2.19 (2H, m), 2.09-2.08 (1H, m), 1.94-1.87 (2H, m), 1.74-1.68 (1H, m), 1.47-1.41 (1H, m); $^{13}$C NMR (150 MHz, MeOD) δ 147.2, 134.4, 134.2, 130.9, 123.3, 120.9, 115.3, 113.9, 58.0, 31.4, 28.8, 28.6, 26.7; LCMS m/z 277.0863 ([M+H$^+$], $C_{19}H_{19}NO$ requires 277.1467).

Using the typical procedure (S)-10-(cyclohept-2-en-1-yl)-10H-phenoxazine (0.473 g, 1.71 mmol) was transformed to (1S,2R,3S)-3-(10H-phenoxazin-10-yl)cycloheptane-1,2-diol (0.409 g, 77%). $^1$H NMR (600 MHz, MeOD) δ 6.87-6.84 (2H, m), 6.78 (2H, d, J=7.8 Hz), 6.74-6.69 (4H, m), 4.34 (1H, dd, J=8.4, 3.0 Hz), 4.03 (1H, d, J=7.8 Hz), 3.94-3.91 (1H, m), 2.17-2.11 (1H, m), 2.00-1.95 (1H, m), 1.85-1.80 (3H, m), 1.66-1.50 (3H, m); $^{13}$C NMR (150 MHz, MeOD) δ 148.0, 135.1, 123.4, 121.3, 115.4, 115.2, 72.7, 72.3, 64.4, 31.1, 29.8, 27.8, 25.2; HPLC analysis: 96% ee (CHIRALPAK IA, 70:30 hexanes-EtOH, 1.0 mL/min, UV: 210 nm), tR=5.81 min (minor), 6.92 min (major); LCMS m/z 312.1293 ([M+H$^+$], $C_{19}H_{22}NO_3$ requires 312.1595).

Using the typical procedure 9H-carbazole (0.334 g, 2.00 mmol) was reacted with tert-butyl 5-((tert-butoxycarbonyl)oxy)-5,6-dihydropyridine-1(2H)-carboxylate (1.44 g, 4.80 mmol) in presence of (S,S)-L1 for 10 days to afford (S)-tert-butyl 5-(9H-carbazol-9-yl)-5,6-dihydropyridine-1(2H)-carboxylate (0.450 g, 65%). $^1$H NMR (600 MHz, MeOD) δ reported as a mixture of rotamers δ 8.07 (2H, d, J=7.8 Hz), 7.58 (2H, d, J=7.8 Hz), 7.37 (2H, br s), 7.18 (2H, t, J=7.2 Hz), 2H [6.24 (br s); 6.13 (br s)], 5.44-5.39 (1H, m), 4.32-4.01 (3H, m), 1H [3.52 (br s); 3.30 (br s)], 9H [1.46 (br s); 1.07 (br s)]; LCMS m/z 249.1408 ([M+H$^+$-Boc], $C_{17}H_{17}N_2$ requires 249.1387).

Using the typical procedure (S)-tert-butyl 5-(9H-carbazol-9-yl)-5,6-dihydropyridine-1(2H)-carboxylate (0.430 g, 1.23 mmol) was transformed to (3R,4S,5R)-tert-butyl 3-(9H-carbazol-9-yl)-4,5-dihydroxypiperidine-1-carboxylate (0.421 g, 89%). $^1$H NMR (600 MHz, MeOD) δ reported as a mixture of rotamers δ 8.08-8.07 (2H, m), 7.71-7.59 (2H, m), 7.41-7.37 (2H, m), 7.20-7.18 (2H, m), 4.96-4.95 (1H, m), 4.71 (1H, d, J=9.6 Hz), 4.36-4.08 (3H, m), 3.71-3.65 (1H, m), 3.28-3.18 (1H, m), 9H [1.50 (br s); 1.43 (br s)]; Material produced in this fashion exhibited [α]$^{25}$D=−3.0° (c=1.0, CH$_3$OH). HPLC analysis: >99% ee (CHIRALPAK IA-3, 80:20:0.1 hexanes-EtOH-diethylamine, 1.0 mL/min, UV: 254 nm), tR=2.36 min; LCMS m/z 283.1349 ([M+H$^+$-Boc], $C_{17}H_{19}N_2O_2$ requires 283.1442).

Example 29 (1S,3S,4R,5S)-methyl 3,4-dihydroxy-5-(10H-phenoxazin-10-yl)cyclohexanecarboxylate

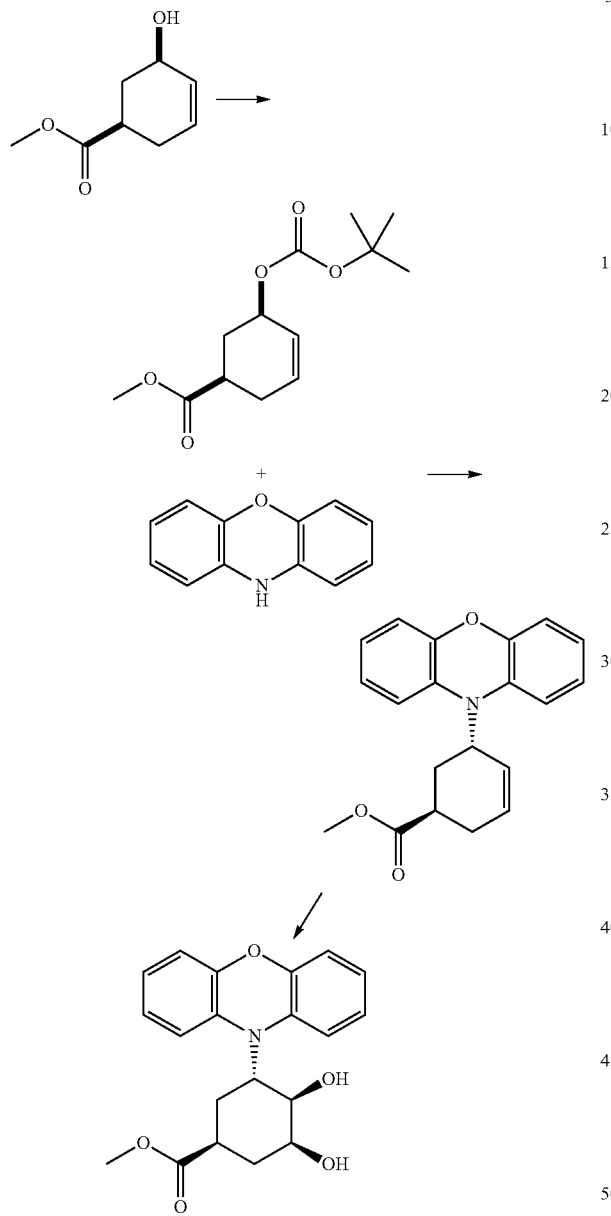

To a solution of (1R,5R)-methyl 5-hydroxycyclohex-3-enecarboxylate (1.00 g, 6.40 mmol) in THF (21.0 mL) cooled to −78° C., n-butyllithium (4.40 mL, 7.04 mmol, 1.6 M in hexanes) was added. The resulting solution was warmed to 0° C. and stirred for 5 min prior to addition of di-tert-butyl dicarbonate (1.54 g, 7.04 mmol) in THF (11.0 mL). The reaction was warmed to RT, stirred for 20 h. The reaction was then quenched with water, extracted with ethyl acetate, washed with brine, concentrated, and the residue was purified by column chromatography (SiO$_2$, 0%-10% ethyl acetate in hexanes) to give (1R,5R)-methyl 5-((tert-butoxycarbonyl)oxy)cyclohex-3-enecarboxylate (0.709 g, 43%).
$^1$H NMR (600 MHz, CDCl$_3$) δ 5.85-5.83 (1H, m), 5.67 (1H, d, J=10.2 Hz), 5.11-5.16 (1H, m), 3.68 (3H, s), 2.72-2.67 (1H, m), 2.42-2.39 (1H, m), 2.28-2.27 (2H, m), 1.80-1.75 (1H, m), 1.47 (9H, br s); $^{13}$C NMR (150 MHz, CDCl$_3$) δ 174.7, 153.2, 129.4, 126.7, 82.3, 72.0, 52.0, 37.9, 30.6, 27.9, 27.4

Using the typical procedure 10H-phenoxazine (0.161 g, 0.883 mmol) was reacted with (1R,5R)-methyl 5-((tert-butoxycarbonyl)oxy)cyclohex-3-enecarboxylate (0.545 g, 2.12 mmol) in presence of (R,R)-L1 for 10 days to afford crude (1R,5S)-methyl 5-(10H-phenoxazin-10-yl)cyclohex-3-enecarboxylate (0.484 g) which was taken to the next step without further purification.

Using the typical procedure (1R,5S)-methyl 5-(10H-phenoxazin-10-yl)cyclohex-3-enecarboxylate (0.400 g, 1.71 mmol) was transformed to (1S,3S,4R,5S)-methyl 3,4-dihydroxy-5-(10H-phenoxazin-10-yl)cyclohexanecarboxylate, which was purified by semi-prep HPLC (XDB-C$_{18}$ column, Acetonitrile-water, gradient), (0.028 g, 7% over two steps).
$^1$H NMR (600 MHz, MeOD) δ 7.02 (2H, d, J=7.8 Hz), 6.90 (2H, t, J=7.8 Hz), 6.82 (2H, d, J=7.8 Hz), 6.75 (2H, d, J=8.4 Hz), 4.17 (1H br s), 4.03 (1H, dd, J=10.8, 2.4 Hz), 3.98-3.94 (1H, m), 3.63 (3H, s), 2.91-2.87 (1H, m), 2.17-2.15 (1H, m), 2.08 (1H, dd, J=13.8, 1.8 Hz), 1.93-1.89 (1H, m), 1.65 (1H, t, J=12.6 Hz); $^{13}$C NMR (150 MHz, MeOD) δ 175.7, 149.8, 135.3, 123.4, 122.6, 119.0, 115.4, 71.7, 69.5, 63.5, 51.1, 36.7, 33.8, 31.0; Material produced in this fashion exhibited [α]$^{25}$D=+33.0° (c=1.0, CH$_3$OH). HRMS m/z 356.1491 ([M+H$^+$], C$_{20}$H$_{22}$NO$_5$ requires 356.1493).

Example 30: (1S,2R,3S)-3-(9H-carbazol-9-yl)cyclopentane-1,2-diol

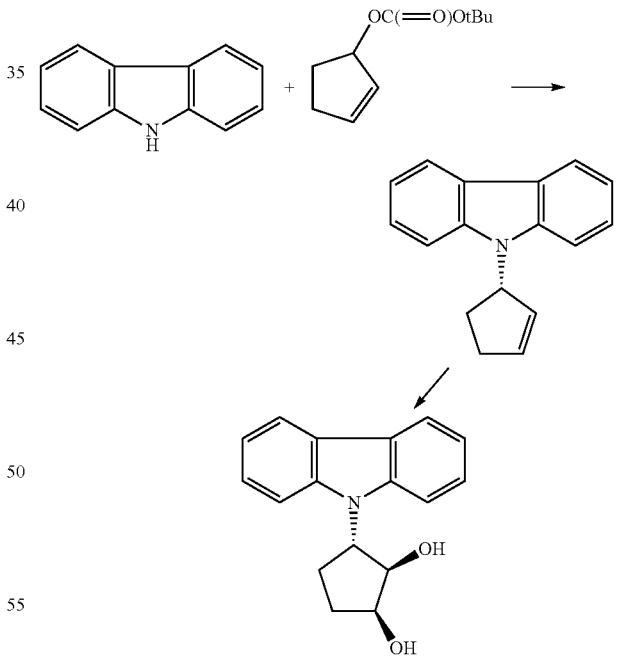

Using the typical procedure 9H-carbazole (0.334 g, 2.00 mmol) was reacted with tert-butyl cyclopent-2-en-1-yl carbonate (0.884 g, 4.80 mmol) in presence of (R,R)-L1 ligand for 10 days to afford (S)-9-(cyclopent-2-en-1-yl)-9H-carbazole (0.449 g, 96%) as a white solid. $^1$H NMR (600 MHz, MeOD) δ 8.05 (2H, d, J=7.8 Hz), 7.52 (2H, d, J=8.4 Hz), 7.35 (2H, td, J=8.4, 1.2 Hz), 7.15 (2H, t, J=7.8 Hz), 6.20-6.18 (1H, m), 6.00-5.94 (2H, m), 2.83-2.78 (1H, m), 2.65-2.61 (1H, m), 2.58-2.52 (1H, m), 2.15-2.10 (1H, m);

$^{13}$C NMR (150 MHz, MeOD) δ 140.2, 134.0, 131.2, 125.1, 123.3, 119.7, 118.6, 109.8, 61.0, 31.7, 27.7; HRMS m/z 234.1278 ([M+H$^+$], C$_{17}$H$_{16}$N requires 234.1278).

Using the typical procedure (S)-9-(cyclopent-2-en-1-yl)-9H-carbazole (0.400 g, 1.71 mmol) was transformed to (1S,2R,3S)-3-(9H-carbazol-9-yl)cyclopentane-1,2-diol (0.386 g, 84%) obtained as a white solid. $^1$H NMR (600 MHz, MeOD) δ 8.07 (2H, d, J=7.8 Hz), 7.53 (2H, d, J=7.8 Hz), 7.40 (2H, d, J=7.8 Hz), 7.17 (2H, d, J=7.2 Hz), 5.25-5.23 (1H, m), 4.79 (1H, dd, J=9.0, 4.2 Hz), 4.25 (1H, br s), 2.38-2.31 (3H, m), 1.97-1.94 (1H, m); $^{13}$C NMR (150 MHz, MeOD) δ 140.1, 125.2, 123.4, 119.8, 118.5, 109.7, 75.1, 72.3, 59.4, 29.0, 22.6; Material produced in this fashion exhibited [α]$^{25}$D=−11.0° (c=1.0, CH$_3$OH). HPLC analysis: 95% ee (CHIRALPAK IF-3, 70:30 hexane:isopropanol, 1.5 mL/min, UV: 254 nm), tR=4.69 min (minor), 3.89 min (major); HRMS m/z 268.1337 ([M+H$^+$], C$_{17}$H$_{18}$NO$_2$ requires 268.1333).

Example 31: (R)-6-(3,6-dihydro-2H-pyran-3-yl)-6H-dibenzo[b,f][1,4,5]oxathiazepine 5,5-dioxide

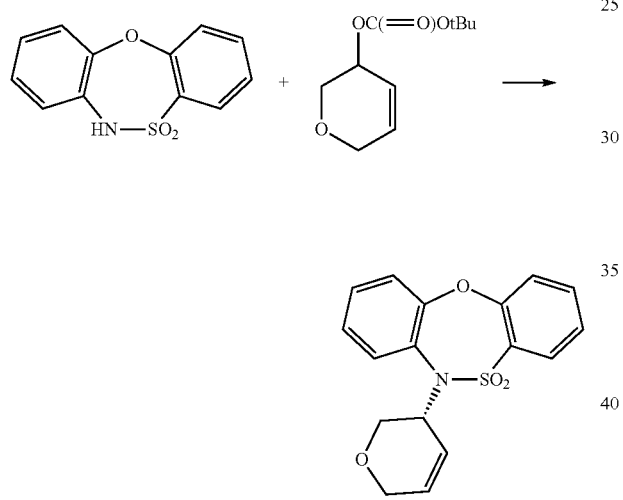

Using the typical procedure 6H-dibenzo[b,f][1,4,5]oxathiazepine 5,5-dioxide (0.494 g, 2.00 mmol) was reacted with tert-butyl (3,6-dihydro-2H-pyran-3-yl) carbonate (0.961 g, 4.80 mmol) in presence of (R,R)-L1 ligand for 10 days to afford (R)-6-(3,6-dihydro-2H-pyran-3-yl)-6H-dibenzo[b,f][1,4,5]oxathiazepine 5,5-dioxide (0.525 g, 80%) obtained as a white solid. $^1$H NMR (600 MHz, MeOD) δ 7.81 (1H, dd, J=7.8, 1.2 Hz), 7.63-7.60 (1H, m), 7.48 (1H, dd, J=7.8, 1.2 Hz), 7.43-7.38 (2H, m), 7.32-7.30 (2H, m), 7.25 (1H, td, J=7.8, 1.2 Hz), 5.87-5.86 (1H, m), 5.73 (1H, br s), 4.56 (1H, s), 4.11-4.09 (1H, m), 3.98-3.95 (1H, m), 3.88-3.84 (2H, m); $^{13}$C NMR (150 MHz, MeOD) δ 134.7, 134.1, 133.4, 132.4, 130.3, 128.1, 126.2, 125.8, 125.1, 124.1, 122.5, 122.3, 121.9, 121.6, 69.3, 64.6, 54.3; Material produced in this fashion exhibited [α]$^{25}$D=−190.0° (c=1.0, CH$_3$OH). HPLC analysis: 91% ee (CHIRALPAK IA, 70:30: 0.1 hexanes-EtOH-diethylamine, 1.0 mL/min, UV: 280 nm), t$_R$=15.17 min (minor), 9.69 min (major); HRMS m/z 330.0796 ([M+H$^+$], C$_{17}$H$_{16}$NO$_4$S requires 330.0795).

An alternative approach to key intermediates in the synthesis of the antineoplastic compounds described in PCT/US2015/019770 proceeds through a rel-(1S,2S,6R)-2-amino-6-(N-attached-sulfonamide)cyclohexane epoxide, but this time the intermediate is of formula X, rather than V:

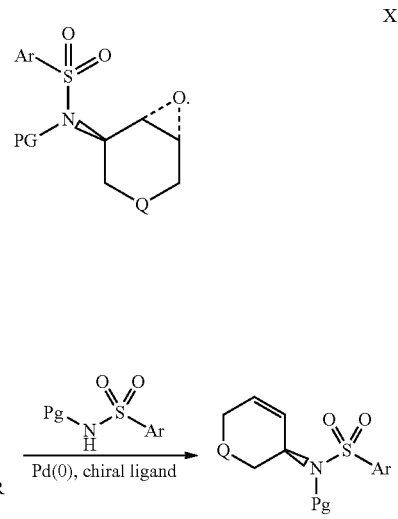

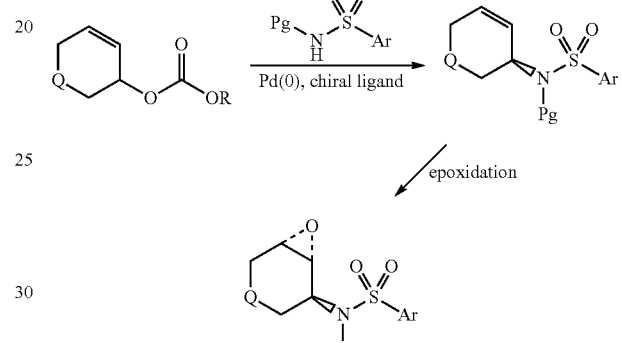

Example 100

A vial is charged with Pd$_2$.dba$_3$. CHCl$_3$ (catalytic, 1 to 5 mole %), and optically pure DACH-phenyl Trost ligand (catalytic 2 to 15 mole %). The vial is sealed, evacuated and backfilled with argon three times. Dry degassed dichloromethane is added to this vial, and the mixture is stirred at room temperature for 30 to 120 min. Racemic tert-butyl (3,6-dihydro-2H-pyran-3-yl) carbonate (1 equiv.), is added to the vial and the contents are transferred to a second vial containing N-benzyl-4-(trifluoromethoxy)benzenesulfonamide, 2 (0.8 to 1.2 equiv), in dry degassed dichloromethane. The reaction mixture was stirred at ambient temperature to 50° C. for between 1 to 10 days. At this point, the reaction mixture is evaporated onto silica gel and subjected to column chromatography to afford optically enriched N-benzyl-N-(3,6-dihydro-2H-pyran-3-yl)-4-(trifluoromethoxy)benzenesulfonamide. The dihydropyran is epoxidized with mCPBA to give optically enriched N-benzyl-N-(3,7-dioxabicyclo[4.1.0]heptan-5-yl)-4-(trifluoromethoxy)benzenesulfonamide, Example 100a, the isomer with 1R,5S,6S relative stereochemistry and 100b, the isomer with 1S,5S,6R relative stereochemistry. Either isomer of compound 100 is converted to an antineoplastic compound of the genus described in PCT/US2015/019770 by treatment with an optionally substituted carbazole or phenoxazine in the presence of a base such as sodium amide, sodium hydride or potassium t-butoxide in an aprotic solvent, followed by mild hydrogenolysis with catalytic palladium on charcoal to remove the benzyl group.

Example 101: tert-butyl (3,6-dihydro-2H-pyran-3-yl)((4-(trifluoro-methoxy)phenyl)sulfonyl)carbamate

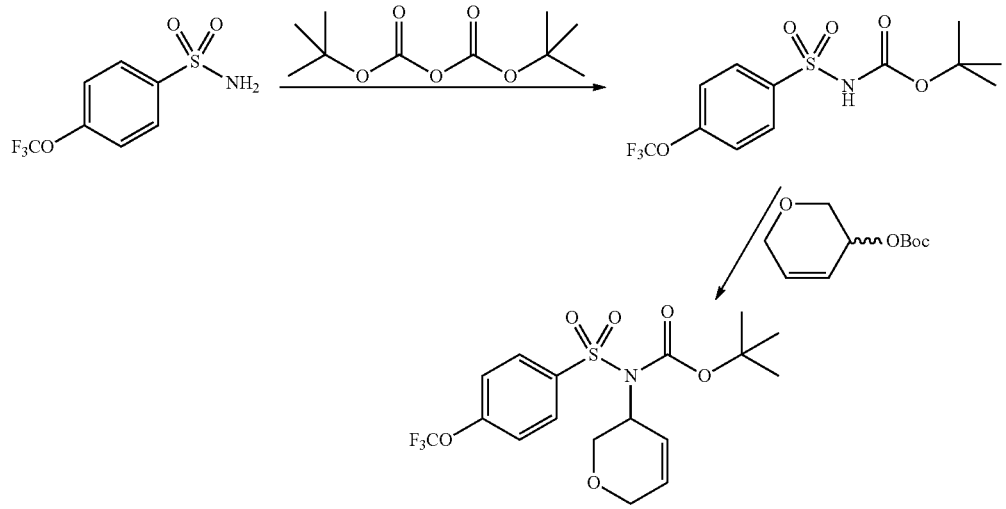

To a solution of 4-(trifluoromethoxy)benzenesulfonamide (0.500 g, 2.07 mmol), Triethylamine (0.318 mL, 2.28 mmol), and DMAP (0.025 g, 0.210 mmol) in DCM (3.00 mL) at 0° C., was added di-tert-butyl dicarbonate (0.498 g, 2.28 mmol) in DCM (3.50 mL). The reaction was stirred at RT for 20 h, washed with 10% aq. sodium bisulfate and brine. Organic layer was concentrated and residue was subjected to column chromatography (SiO$_2$, 10%-33% ethyl acetate in hexanes) to afford tert-butyl (4-(trifluoromethoxy)phenyl)sulfonylcarbamate (0.491 g, 69%). $^1$H NMR (600 MHz, CDCl$_3$) δ 8.09 (2H, d, J=9.0 Hz), 7.98 (1H, br s), 7.36 (2H, d, J=8.4 Hz), 1.38 (9H, br s); $^{13}$C NMR (150 MHz, CDCl$_3$) δ 153.0, 149.3, 137.2, 130.7, 120.8, 84.7, 28.0; LCMS m/z 286.0072 ([M+H$^+$−t-Bu], C$_8$H$_7$F$_3$NO$_5$S requires 285.9992).

bonate (0.678 g, 3.38 mmol) in presence of triphenylphosphine for 10 days to afford tert-butyl (3,6-dihydro-2H-pyran-3-yl)((4-(trifluoromethoxy)phenyl)sulfonyl)carbamate (0.198 g, 33%). $^1$H NMR (600 MHz, MeOD) δ 8.08 (2H, d, J=9.0 Hz), 7.51 (2H, d, J=8.4 Hz), 5.85 (1H, d, J=10.2 Hz), 5.69 (1H, d, J=10.2 Hz), 5.16 (1H, br s), 4.11-4.10 (2H, m), 4.01-4.00 (2H, m), 1.36 (9H, br s); $^{13}$C NMR (150 MHz, MeOD) δ 152.6, 150.3, 139.0, 130.4, 127.5, 125.6, 120.9, 85.1, 66.0, 64.6, 52.6, 26.8; LCMS m/z 368.1665 ([M+H$^+$−t-Bu], C$_{13}$H$_{13}$F$_3$NO$_6$S requires 368.0411).

Example 102: N-benzyl-N-(3,6-dihydro-2H-pyran-3-yl)-4-(trifluoromethoxy)benzenesulfonamide

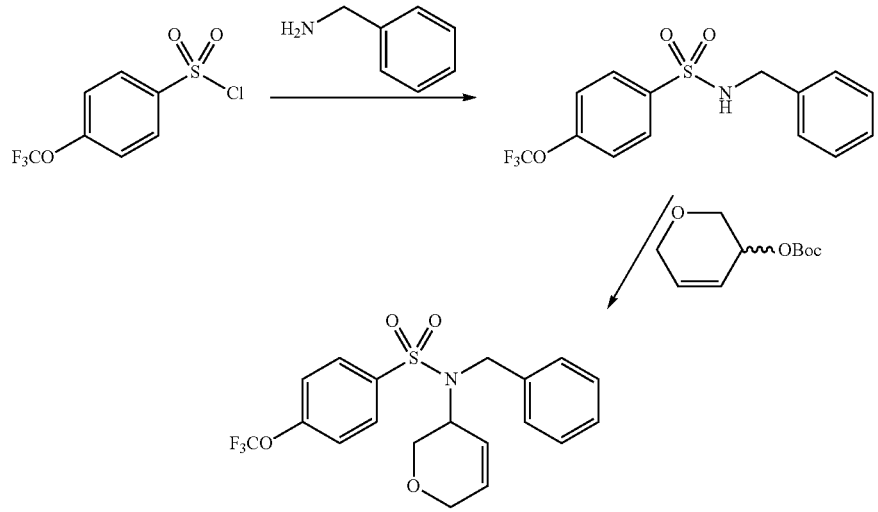

Using the typical procedure tert-butyl (4-(trifluoromethoxy)-phenyl)sulfonylcarbamate (0.482 g, 1.41 mmol) was reacted with tert-butyl (3,6-dihydro-2H-pyran-3-yl) car- A solution of phenylmethanamine (0.750 g, 6.99 mmol) and triethylamine (3.89 mL, 27.9 mmol) in DMF (6.0 mL) was cooled in an ice bath below 5° C. 4-(trifluoromethoxy)

benzene-1-sulfonyl chloride (2.01 g, 7.69 mmol) was added slowly to the mixture. The mixture was warmed to RT, and stirred for 1 h. The reaction mixture was then poured into water and extracted with ethyl acetate. The combined organic layer was washed with brine. The solvent was removed under reduced pressure and residue was subjected to column chromatography ($SiO_2$, 10%-17% ethyl acetate in hexanes) to afford N-benzyl-4-(trifluoromethoxy)benzenesulfonamide (0.926 g, 40%). $^1$H NMR (600 MHz, $CDCl_3$) δ 7.88 (2H, d, J=6.6 Hz), 7.31-7.17 (7H, m), 4.82 (1H, s), 4.19 (2H, d, J=4.2 Hz); $^{13}$C NMR (150 MHz, $CDCl_3$) δ 152.2, 138.6, 136.0, 129.4, 128.8, 128.1, 128.0, 121.1, 47.4; LCMS m/z 332.0554 ([M+H$^+$], $C_{14}H_{13}F_3NO_3S$ requires 332.0563).

Using the typical procedure N-benzyl-4-(trifluoromethoxy)benzenesulfonamide (0.663 g, 2.00 mmol) was reacted with tert-butyl (3,6-dihydro-2H-pyran-3-yl) carbonate (0.961 g, 4.80 mmol) in presence of triphenylphosphine for 10 days to afford N-benzyl-N-(3,6-dihydro-2H-pyran-3-yl)-4-(trifluoromethoxy)benzenesulfonamide (0.795 g, 96%). $^1$H NMR (600 MHz, MeOD) δ 7.88 (2H, d, J=9.0 Hz), 7.41 (2H, d, J=8.4 Hz), 7.31 (2H, d, J=7.2 Hz), 7.25-7.18 (3H, m), 5.91 (1H, d, J=10.2 Hz), 5.41 (1H, d, J=10.2 Hz), 4.65-4.62 (1H, m), 4.47-4.43 (2H, m), 3.97-3.90 (2H, m), 3.69 (1H, dd, J=11.4, 4.2 Hz), 3.55 (1H, dd, J=12.0 3.6 Hz); $^{13}$C NMR (150 MHz, MeOD) δ 152.0, 140.0, 138.6, 132.0, 129.3, 127.9, 127.0, 123.0, 121.2, 119.6, 68.1, 64.5, 51.6, 48.4; HPLC analysis: (CHIRALPAK IA-3, 70:30 hexanes-EtOH-diethylamine, 1.0 mL/min, UV: 254 nm), tR=2.76 min, 5.31 min; HRMS m/z 414.0989 ([M+H$^+$], $C_{19}H_{19}F_3NO_4S$ requires 414.0982).

Example 103 (single enantiomer of Example 102): (R)—N-benzyl-N-(3,6-dihydro-2H-pyran-3-yl)-4-(trifluoromethoxy)benzenesulfonamide

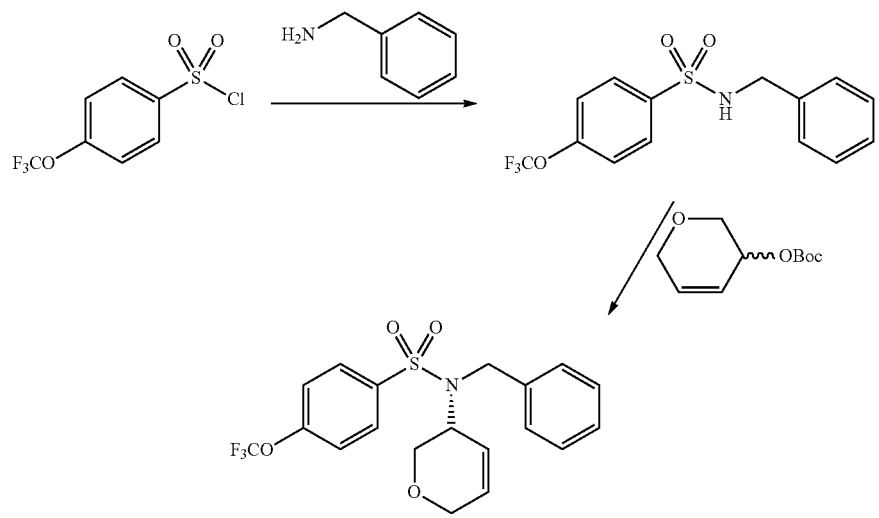

Using the typical procedure N-benzyl-4-(trifluoromethoxy)benzenesulfonamide (0.200 g, 0.603 mmol) was reacted with tert-butyl (3,6-dihydro-2H-pyran-3-yl) carbonate (0.289 g, 1.45 mmol) in presence of (R,R)-L1 for 10 days to afford (R)—N-benzyl-N-(3,6-dihydro-2H-pyran-3-yl)-4-(trifluoromethoxy)benzenesulfonamide (0.228 g, 92%). $^1$H NMR (600 MHz, MeOD) δ 7.89 (2H, d, J=8.4 Hz), 7.43 (2H, d, J=8.4 Hz), 7.32 (2H, d, J=7.2 Hz), 7.26-7.20 (3H, m), 5.93 (1H, d, J=10.2 Hz), 5.41 (1H, d, J=10.2 Hz), 4.66-4.63 (1H, m), 4.48-4.44 (2H, m), 3.98-3.91 (2H, m), 3.70 (1H, dd, J=12.0, 4.2 Hz), 3.55 (1H, dd, J=12.0 3.6 Hz); $^{13}$C NMR (150 MHz, MeOD) δ 152.0, 140.0, 138.6, 132.0, 129.3, 127.9, 127.0, 123.0, 121.2, 119.6, 68.1, 64.5, 51.6, 48.3; HPLC analysis: (CHIRALPAK IA-3, 70:30 hexanes-EtOH-diethylamine, 1.0 mL/min, UV: 254 nm), tR=2.72 min (minor), 5.10 min (major); HPLC analysis: >94% ee Material produced in this fashion exhibited [α]$^{25}$D=−93.0° (c=1.0, $CH_3OH$); HRMS m/z 414.0989 ([M+H$^+$], $C_{19}H_{19}F_3NO_4S$ requires 414.0988).

The invention claimed is:
1. A process for preparing a substantially enantiomerically pure compound of formula (I):

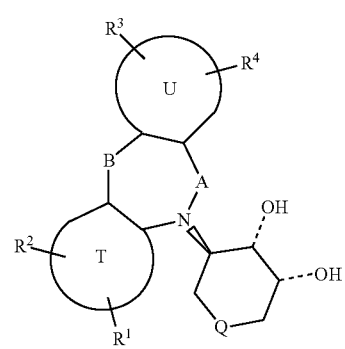

wherein:
A is selected from the group consisting of a direct bond, —$SO_2$—, and —C(=O)—;
B is selected from the group consisting of a direct bond, —O—, —SO— and —$SO_2$—;
T is a benzene ring or a five or six membered heteroaromatic ring;
U is a benzene ring or a five or six membered heteroaromatic ring; and
$R^1$, $R^2$, $R^3$ and $R^4$ are chosen independently from H, OH, halogen, cyano, nitro, ($C_1$-$C_3$)alkylamino, ($C_1$-$C_3$)dialkylamino, ($C_1$-$C_3$)acylamino, ($C_1$-$C_3$)alkylsulfonyl, ($C_1$-$C_3$)alkylthio, ($C_1$-$C_3$)alkyl, ($C_1$-$C_3$)haloalkyl, ($C_1$-

$C_3$)haloalkoxy, ($C_1$-$C_3$)haloalkylthio, —CC(=O)O($C_1$-$C_3$)alkyl, and ($C_1$-$C_3$)alkoxy;

Q is chosen from direct bond, —$CH_2$—, —$CH_2CH_2$—, —O—, —CH(OH)—, —CH(COOR$^5$)—, —CH(CONR'R")—, —CH($CH_2$)NR'R", —CH(CN)—, —S(O)$_n$—, —CH(NHBoc), —CH(NHCBZ), —NR$^6$—,

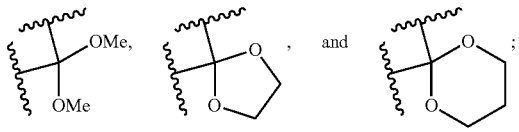 [SMILES: *C(*)(OC)OC ; *C1(*)OCCO1 ; *C1(*)OCCCO1]

$R^5$ is H or ($C_1$-$C_4$)alkyl;

$R^6$ is chosen from ($C_1$-$C_4$)alkyl, ($C_1$-$C_4$)acyl, ($C_4$-$C_7$) alkoxycarbonyl, and benzyloxycarbonyl;

R' and R" are independently chosen from H, lower alkyl, substituted alkyl, aryl, substituted aryl; or R' and R" together with the nitrogen to which they are attached, may form an optionally substituted heterocyclic ring;

said process comprising:

(a) reacting a compound of formula II

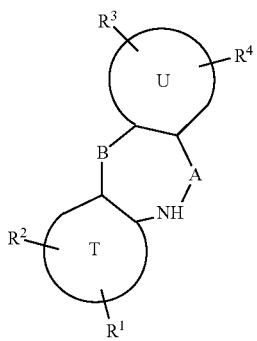

II with a compound of formula III

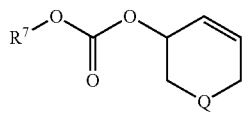

III wherein R$^7$ is ($C_1$-$C_4$)alkyl, in the presence of a chiral palladium catalyst to provide a product of formula IV

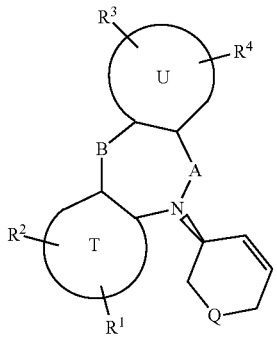

IV and (b) oxidizing said product of formula IV with osmium tetroxide to provide I.

2. The process of claim 1 wherein said compounds II and III are reacted in the presence of a chiral palladium catalyst formed from a chiral ligand and a palladium compound chosen from tris(dibenzylideneacetone)dipalladium, bis(dibenzylideneacetone)palladium, tetrakis(triphenylphosphine)palladium, and allylpalladium chloride dimer.

3. The process of claim 2 wherein said chiral ligand is chosen from (2,2'-bis(diphenylphosphino)-1,1'-binaphthyl) (BINAP), 5,5'-bis(diphenylphosphino)-4,4'-bi-1,3-benzodioxole (SEGPHOS), 1,2-diaminocyclohexane-N,N'-bis(2-diphenylphosphinobenzoyl) (DACH-phenyl), and 1,2-diaminocyclohexane-N,N'-bis(2-diphenylphosphino-1-naphthoyl) (DACH-naphthyl).

4. The process of claim 1 wherein one of rings T and U is benzene and the other is pyridine, pyrimidine or thiene.

5. The process of claim 1 wherein both of rings T and U are benzene.

6. The process of claim 1, wherein Q is chosen from —$CH_2$—, —O—, —N(Boc)-, —N(Cbz)-, —N($CH_3$)—, and —N(Ac)-.

7. The process of claim 1 wherein A is a direct bond.

8. The process of claim 2 wherein said chiral palladium catalyst is derived from tris(dibenzylideneacetone)dipalladium and a chiral ligand containing the trans-1,2-diaminocyclohexane (DACH) moiety.

9. The process of claim 1 wherein said compound IV is oxidized with osmium tetroxide in the presence of 4-methylmorpholine N-oxide.

10. The process of claim 1 wherein $R^1$, $R^2$, $R^3$ and $R^4$ are chosen independently from H, F, Cl, $CH_3$, $NO_2$, $CF_3$, $OCF_3$, $OCH_3$, and $SCF_3$.

11. The process of claim 10 wherein three of R', $R^2$, $R^3$ and $R^4$ are H and the fourth is chosen from H, F, Cl, $CH_3$, $NO_2$, $CF_3$, $OCF_3$, $OCH_3$, and $SCF_3$.

12. The process of claim 1 wherein A is $SO_2$.

* * * * *